United States Patent
Metcalfe et al.

(10) Patent No.: US 12,178,515 B2
(45) Date of Patent: Dec. 31, 2024

(54) SYSTEMS AND METHODS FOR DENSITY CALIBRATION

(71) Applicant: Arthrex, Inc., Naples, FL (US)

(72) Inventors: Nick Metcalfe, Bonita Springs, FL (US); Robert Fergan, Naples, FL (US); David Knopf, Bonita Springs, FL (US)

(73) Assignee: ARTHREX, INC., Naples, FL (US)

( * ) Notice: Subject to any disclaimer, the term of this patent is extended or adjusted under 35 U.S.C. 154(b) by 478 days.

(21) Appl. No.: 17/691,364

(22) Filed: Mar. 10, 2022

(65) Prior Publication Data

US 2022/0338930 A1 Oct. 27, 2022

Related U.S. Application Data

(60) Provisional application No. 63/179,729, filed on Apr. 26, 2021.

(51) Int. Cl.
*A61B 34/10* (2016.01)
*A61B 6/03* (2006.01)
(Continued)

(52) U.S. Cl.
CPC ............. *A61B 34/10* (2016.02); *A61B 6/032* (2013.01); *A61B 6/405* (2013.01); *A61B 6/463* (2013.01);
(Continued)

(58) Field of Classification Search
CPC ........... A61B 34/10; A61B 34/25; A61B 6/00; A61B 6/03; A61B 6/032; A61B 6/405; A61B 6/463; A61B 6/505; A61B 6/563; A61B 6/566; A61B 6/583; A61B 2017/00712; A61B 2017/00725; A61B 2034/102; A61B 2034/105; A61B 2034/108; A61B 2034/256; G16H 20/40; G16H 30/40; G16H 30/20; G16H 40/40; G16H 40/63; G16H 40/67
See application file for complete search history.

(56) References Cited

U.S. PATENT DOCUMENTS 5,824,085 A 10/1998 Sahay et al.
6,917,827 B2 7/2005 Kienzle, III
(Continued)

FOREIGN PATENT DOCUMENTS

WO 2005089681 9/2005
WO 2010068212 6/2010
(Continued)

OTHER PUBLICATIONS

Brochure. Tornier Blueprint 3D Planning + PSI: Surgical Technique v.2.1—Polyamide. Wright Focused Excellence. Feb. 2017. Retrieved from: http://www.wrightemedia.com/ProductFiles/Files/PDFs/CAW-8609_EN_HR_LE.pdf.
(Continued)

*Primary Examiner* — Jurie Yun
(74) *Attorney, Agent, or Firm* — Carlson, Gaskey & Olds, P.C.

(57) ABSTRACT

This disclosure relates to planning systems and methods. The planning systems and methods disclosed herein may be utilized for planning orthopaedic procedures to restore functionality to a joint, and may include one or more calibration objects for calibrating images of patient anatomy.

17 Claims, 19 Drawing Sheets

(51) Int. Cl.
  *A61B 6/40* (2024.01)
  *A61B 6/46* (2024.01)
  *A61B 6/58* (2024.01)
  *G16H 20/40* (2018.01)
  *G16H 30/40* (2018.01)

(52) U.S. Cl.
  CPC ............ *A61B 6/583* (2013.01); *G16H 20/40* (2018.01); *G16H 30/40* (2018.01); *A61B 2034/102* (2016.02)

(56) References Cited

U.S. PATENT DOCUMENTS

| | | | |
|---|---|---|---|
| 7,194,295 B2 | 3/2007 | Vilsmeier |
| 7,467,892 B2 | 12/2008 | Lang et al. |
| 7,599,468 B2 | 10/2009 | Zuendorf et al. |
| 8,160,325 B2 | 4/2012 | Zug et al. |
| 8,214,016 B2 | 7/2012 | Lavallee et al. |
| 8,331,634 B2 | 12/2012 | Barth et al. |
| 8,382,765 B2 | 2/2013 | Axelson et al. |
| 8,706,197 B2 | 4/2014 | Henning et al. |
| 8,731,885 B2 | 5/2014 | Iannotti et al. |
| 8,831,319 B2 | 9/2014 | Dafni et al. |
| 9,173,665 B2 | 11/2015 | Couture |
| 9,211,199 B2 | 12/2015 | Ratron |
| 9,299,138 B2 | 3/2016 | Zellner et al. |
| 9,498,234 B2 | 11/2016 | Goldstein et al. |
| 9,684,768 B2 | 6/2017 | Lavallee et al. |
| 9,741,263 B2 | 8/2017 | Iannotti et al. |
| 10,016,177 B2 | 7/2018 | Aram et al. |
| 10,070,928 B2 | 9/2018 | Frank et al. |
| 10,102,309 B2 | 10/2018 | McKinnon et al. |
| 10,159,530 B2 | 12/2018 | Lang |
| 10,172,675 B2 | 1/2019 | Mahfouz |
| 10,172,677 B2 | 1/2019 | Wentorf et al. |
| 10,176,642 B2 | 1/2019 | Tran et al. |
| 10,194,991 B2 | 2/2019 | Bonny et al. |
| 10,251,705 B2 | 4/2019 | Kumar et al. |
| 10,292,770 B2 | 5/2019 | Ryan et al. |
| 10,314,653 B2 | 6/2019 | Ikits et al. |
| 10,390,887 B2 | 8/2019 | Bischoff et al. |
| 10,470,821 B2 | 11/2019 | Jaramaz et al. |
| 10,537,390 B2 | 1/2020 | Varadarajan et al. |
| 10,575,875 B2 | 3/2020 | Pavlovskaia et al. |
| 10,624,655 B2 | 4/2020 | Iannotti et al. |
| 10,660,709 B2 | 5/2020 | Chaoui |
| 10,687,856 B2 | 6/2020 | Park et al. |
| 10,705,677 B2 | 7/2020 | Andersson et al. |
| 10,736,697 B2 | 8/2020 | Chaoui et al. |
| 10,828,110 B1 | 11/2020 | Merette et al. |
| 11,113,811 B2 * | 9/2021 | Min .................... A61B 6/5205 |
| 11,246,558 B2 * | 2/2022 | Uber, III ................ A61B 6/545 |
| 2004/0102866 A1 | 5/2004 | Harris et al. |
| 2005/0038338 A1 | 2/2005 | Bono et al. |
| 2005/0256389 A1 | 11/2005 | Koga et al. |
| 2007/0066917 A1 | 3/2007 | Hodorek et al. |
| 2007/0179626 A1 | 8/2007 | de la Barrera et al. |
| 2007/0191741 A1 | 8/2007 | Tsai et al. |
| 2008/0033571 A1 | 2/2008 | Tuke |
| 2008/0058945 A1 | 3/2008 | Hajaj et al. |
| 2009/0089034 A1 | 4/2009 | Penney et al. |
| 2010/0030231 A1 | 2/2010 | Revie et al. |
| 2014/0324182 A1 | 10/2014 | Graumann et al. |
| 2015/0257727 A1 | 9/2015 | Anitua Aldecoa |
| 2016/0045317 A1 | 2/2016 | Lang et al. |
| 2017/0367764 A1 | 12/2017 | Zuhars et al. |
| 2018/0153624 A1 | 6/2018 | Hughes et al. |
| 2018/0289423 A1 | 10/2018 | Singh et al. |
| 2018/0358120 A1 | 12/2018 | Schoenefeld et al. |
| 2018/0360544 A1 | 12/2018 | Vanheule et al. |
| 2019/0046326 A1 | 2/2019 | Ball |
| 2019/0105169 A1 | 4/2019 | Sperling |
| 2019/0175277 A1 | 6/2019 | Chav et al. |
| 2019/0380792 A1 | 12/2019 | Poltaretskyi et al. |
| 2020/0030034 A1 | 1/2020 | Kontaxis et al. |
| 2020/0074748 A1 | 3/2020 | de Almeida Barreto et al. |
| 2020/0205898 A1 | 7/2020 | Hampp et al. |
| 2020/0205900 A1 | 7/2020 | Buckland et al. |

FOREIGN PATENT DOCUMENTS

| | | |
|---|---|---|
| WO | 2013166606 | 11/2013 |
| WO | 2017204832 | 11/2017 |
| WO | 2019148154 | 8/2019 |
| WO | 2020102886 | 5/2020 |
| WO | 2020163328 | 8/2020 |

OTHER PUBLICATIONS

Magosch, P., Habermeyer, P., Bachmaier, S., Metcalfe, N. (2012). Biomechanical basics of the metaphyseal anchored humeral head replacement. Springer-Verlag. 2012. pp. 1-6. (Machine translation—Google).

Riviere, C., Grappiolo, G., Engh, Jr., C.A., Vidalain, J-P., Chen, A-F., Boehler, N., Matta, J., Vendittoli, P-A. (2018). Long-term bone remodelling around 'legendary' cementless femoral stems. Effort Open Reviews. vol. 3. Feb. 2018. pp. 46-57.

\* cited by examiner

SYSTEMS AND METHODS FOR DENSITY CALIBRATION

CROSS REFERENCE TO RELATED APPLICATION

The present disclosure claim priority to U.S. Provisional Application No. 63/179,729 filed Apr. 26, 2021.

BACKGROUND

This disclosure relates to orthopaedic procedures and, more particularly, to systems and methods for planning the repair of bone defects and restoration of functionality to a joint, including calibrating images of patient anatomy and determining density of tissue such as bone.

Many bones of the human musculoskeletal system include articular surfaces. The articular surfaces articulate relative to other bones to facilitate different types and degrees of joint movement. The articular surfaces can erode or experience bone loss over time due to repeated use or wear or can fracture as a result of a traumatic impact. These types of bone defects can cause joint instability and pain.

Bone deficiencies may occur along the articular surfaces. Some techniques utilize a bone graft and/or implant to repair a defect adjacent the articular surfaces. The surgeon may consider bone density and quality of the patient anatomy in selecting an implant and determining placement of the implant. Bone density may be performed utilizing a bone density scan.

SUMMARY

This disclosure relates to planning systems and methods. The planning systems and methods disclosed herein may be utilized for planning orthopaedic procedures to restore functionality to a joint. One or more calibration objects may be utilized for calibrating images of patient anatomy.

A calibration object for calibrating images of anatomy of the present disclosure may include a plurality of density members formed with a main body such that the plurality of density members are distributed in an array along the main body. A volume of each of the density members and the main body may correspond to a respective radiodensity. The radiodensity of two or more of the density members may differ from each other.

A system for calibrating images of anatomy of the present disclosure may include a calibration object and an imaging system. The calibration object may include a plurality of density members formed with a main body. A volume of each of the density members and the main body may correspond to a respective predetermined radiodensity value. The imaging system may include a computing device including a processor coupled to memory. The processor may be configured to execute a planning environment including a data module, a display module and a comparison module. The data module may be configured to receive data corresponding to at least one image of a patient anatomy together with the calibration object from an imaging device. The comparison module may be configured to determine one or more image gradients. Each of the one or more image gradients may be based on a comparison of a pixel value at a respective position in the at least one image and a pixel value at one or more respective positions along the density members in the at least one image. The comparison module may be configured to assign a radiodensity value to one or more positions in the at least one image based upon a comparison of the respective one or more image gradients and each respective predetermined radiodensity value. The display module may be configured to display in a graphical user interface the at least one image and a visual gradient superimposed on the one or more positions according to the assigned radiodensity values. The visual gradient may be defined by the predetermined radiodensity values associated with the density members.

A method for calibrating images of anatomy of the present disclosure may include printing a calibration object. The calibration object may include a plurality of density members having radiodensities corresponding to respective predetermined radiodensity values. The method may include positioning the calibration object in a scan field of an imaging device, capturing, by the imaging device, at least one image of a patient anatomy together with the calibration object in the scan field, and determining one or more image gradients. Each of the one or more image gradients may be based on a comparison of a pixel value at a respective position in the at least one image and a pixel value at one or more respective positions along the density members in the at least one image. The method may include comparing the respective one or more image gradients to each respective predetermined radiodensity value, assigning a radiodensity value to one or more positions in the at least one image based upon the comparing, and displaying in a graphical user interface at least one indicator relating to the assigned radiodensity values.

The various features and advantages of this disclosure will become apparent to those skilled in the art from the following detailed description. The drawings that accompany the detailed description can be briefly described as follows.

BRIEF DESCRIPTION OF THE DRAWINGS

Like reference numbers and designations in the various drawings indicate like elements.

DETAILED DESCRIPTION

Figure 1:
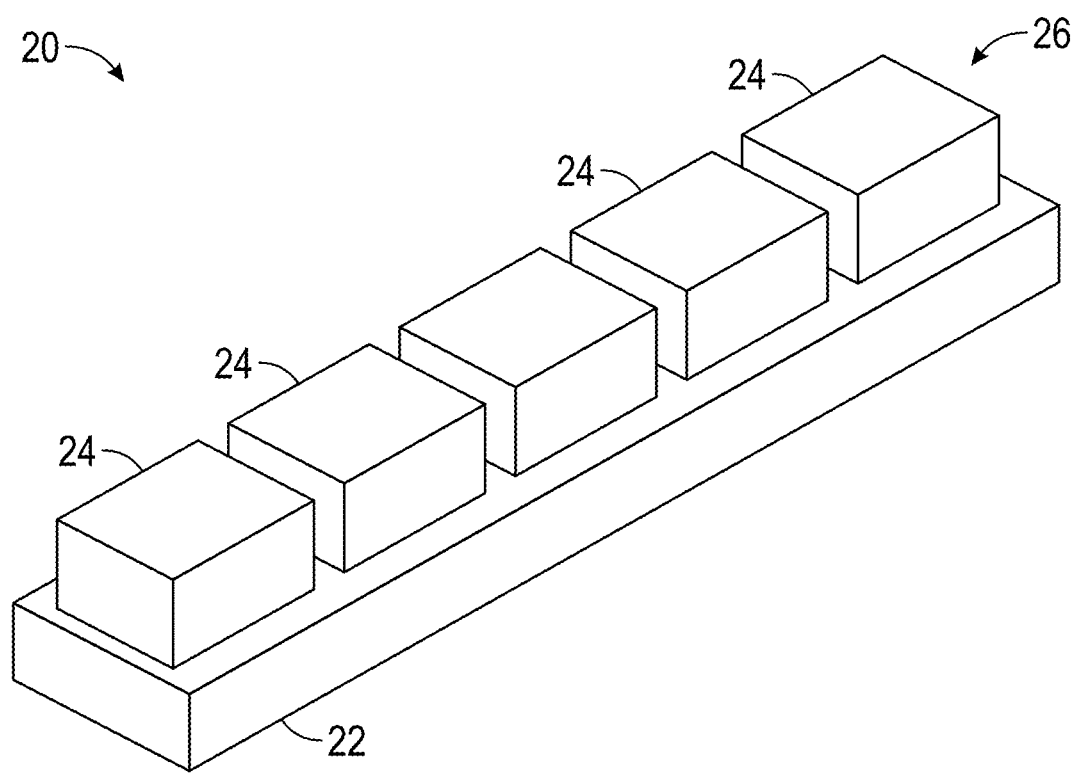
FIGS. 1-3 illustrates an exemplary calibration object.

This disclosure relates to surgical planning, including calibration of images of patient anatomy. The calibrated images may be utilized to determine or infer bone quality and/or bone density.

Information pertaining to bone quality and density may be valuable both pre-operatively and post-operatively for various reasons. Pre-operatively, this information may assist a surgeon in preparing a surgical plan. The surgical plan may include various, such as selection of a suitable procedure, implant type and implant placement. This information may assist the surgeon in establishing a surgical plan by planning to prepare for any relatively low-density regions of bone and other tissue that may cause implant subsidence.

Post-operatively (e.g., day of surgery and then at follow up intervals), this information may assist the surgeon in determining specific regions of bone that may change in bone quality and/or density, including regions that may be load bearing under muscular tension or skeletal load which may remodel after implant placement. Remodeling may include resorption, stress shielding, and implant movement caused by subsidence.

Utilizing the techniques disclosed herein, remodeling may be observed and compared, and predictions may be made as to what treatment intervention may be suitable to reduce a likelihood of relatively more severe complications such as periprosthetic fracturing. These changes may be utilized to identify rehabilitation techniques, implant placement, and future procedures by indicating regions of increased bone growth (e.g., higher load) and/or bone resorption (e.g., lower load).

The planning systems described herein may be utilized for orthopaedic procedures and may be utilized to create, edit, execute and/or review surgical plans. One or more calibration objects may be utilized for calibrating images of patient anatomy in preparation and review of the surgical plans. The calibrated images may be utilized to more accurately determine or infer the density of various tissue at the surgical site, which may be utilized in selection of a suitable treatment including implant selection and placement, which may lead to improved healing of the patient.

A calibration object for calibrating images of anatomy of the present disclosure may include a plurality of density members formed with a main body such that the plurality of density members are distributed in an array along the main body. A volume of each of the density members and the main body may correspond to a respective radiodensity. The radiodensity of two or more of the density members may differ from each other.

In some embodiments, the volume of the main body may be substantially radiolucent.

In some embodiments, the plurality of density members may include three or more density members. The radiodensity of each volume of the density members and the main body may correspond to a respective predetermined radiodensity value. The predetermined radiodensity values of the density members may be within and distributed along a predetermined radiodensity range. The predetermined radiodensity value of the main body may be less than a minimum value of the predetermined radiodensity range.

In some embodiments, the minimum value of the predetermined radiodensity range may be greater than or equal to about 300.0 Hounsfield Units (HU).

In some embodiments, the three or more density members may include a first density member and a second density member at opposed ends of the array. The predetermined radiodensity value of the first density member may correspond to the minimum value of the predetermined radiodensity range. The predetermined radiodensity value of the second density member may correspond to a maximum value of the predetermined radiodensity range.

In some embodiments, the minimum value may be equal to about 300.0 HU. The maximum value may be equal to about 1800.0 HU.

In some embodiments, the volume of each respective density member may have a substantially uniform radiodensity.

In some embodiments, the calibration object may have a monolithic construction established by a plurality of layers. The main body may include an external wall surrounding the density members. The main body may include one or more partitions that span between opposed sides of the external wall to space apart adjacent pairs of the density members.

In some embodiments, the plurality of layers may be arranged in a stacked relationship to establish the main body and the plurality of density members. One or more of the layers may include regions of different radiodensities establishing the respective layer.

In some embodiments, each of the density members may include a porous scaffold having an interconnected network of branches and nodes extending throughout the volume of the respective density member.

In some embodiments, the predetermined radiodensity values of the density members may be within and distributed along a predetermined radiodensity range having a minimum value and a maximum value. The predetermined radiodensity value of the main body may be less than the minimum value of the predetermined radiodensity range. The predetermined radiodensity range may encompass a first radiodensity value of about 300.0 HU and a second radiodensity value of about 1800.0 HU. A difference between the predetermined radiodensity values of each adjacent pair of the density members may be at least 10% of a difference between the maximum value and the minimum value.

A system for calibrating images of anatomy of the present disclosure may include a calibration object and an imaging system. The calibration object may include a plurality of density members formed with a main body. A volume of each of the density members and the main body may correspond to a respective predetermined radiodensity value. The imaging system may include a computing device including a processor coupled to memory. The processor may be configured to execute a planning environment including a data module, a display module and a comparison module. The data module may be configured to receive data corresponding to at least one image of a patient anatomy together with the calibration object from an imaging device. The comparison module may be configured to determine one or more image gradients. Each of the one or more image gradients may be based on a comparison of a pixel value at a respective position in the at least one image and a pixel value at one or more respective positions along the density members in the at least one image. The comparison module may be configured to assign a radiodensity value to one or more positions in the at least one image based upon a comparison of the respective one or more image gradients and each respective predetermined radiodensity value. The display module may be configured to display in a graphical user interface the at least one image and a visual gradient superimposed on the one or more positions according to the assigned radiodensity values. The visual gradient may be defined by the predetermined radiodensity values associated with the density members.

In some embodiments, the at least one image may be an X-ray image.

In some embodiments, the imaging device may be a computerized tomography (CT) machine.

In some embodiments, the visual gradient may be a color gradient in which respective color values are assigned with respect to the predetermined radiodensity values of the density members.

In some embodiments, the display module may be configured to display in the graphical user interface a histogram graph comprising a frequency of the assigned radiodensity values corresponding to at least a subset of the one or more positions in the at least one image.

In some embodiments, the at least one image may include a first image and a second image acquired subsequent to the first image. The comparison module may be configured to determine a difference between the assigned radiodensity values of the one or more positions in the first image and the second image. The display module may be configured to display in the graphical user interface at least one indicator superimposed on the one or more positions in the second image according to the difference in the assigned radiodensity values.

In some embodiments, the display module may be configured to filter from the visual gradient any of the assigned radiodensity values below at least one predetermined threshold.

In some embodiments, the plurality of density members may be distributed in an array along the main body.

In some embodiments, the density members may include three or more density members, the respective predetermined radiodensity values being within a predetermined radiodensity range. The predetermined radiodensity range may be greater than or equal to about 300.0 HU, and may be less than or equal to about 1800.0 HU.

In some embodiments, the calibration object may include a pair of registration members that may be established on opposed sides of the array of the density members. The planning environment may include a spatial module configured to determine the one or more respective positions along the density members in the at least one image in response to identifying respective positions of the pair of registration members in the at least one image.

A method for calibrating images of anatomy of the present disclosure may include printing a calibration object. The calibration object may include a plurality of density members having radiodensities corresponding to respective predetermined radiodensity values. The method may include positioning the calibration object in a scan field of an imaging device, capturing, by the imaging device, at least one image of a patient anatomy together with the calibration object in the scan field, and determining one or more image gradients. Each of the one or more image gradients may be based on a comparison of a pixel value at a respective position in the at least one image and a pixel value at one or more respective positions along the density members in the at least one image. The method may include comparing the respective one or more image gradients to each respective predetermined radiodensity value, assigning a radiodensity value to one or more positions in the at least one image based upon the comparing, and displaying in a graphical user interface at least one indicator relating to the assigned radiodensity values.

In some embodiments, the calibration object may include a pair of registration members that may be established at predetermined positions relative to the radiodensity members. The method may include determining the one or more respective positions along the density members in the at least one image in response to identifying respective positions of the pair of registration members in the at least one image.

In some embodiments, the method may include displaying in a graphical user interface the at least one image and the at least one indicator. The at least one indicator may be a visual gradient superimposed on the one or more positions along the patient anatomy according to the assigned radiodensity values. The visual gradient may be defined by the predetermined radiodensity values associated with the density members.

In some embodiments, the method may include positioning a selected implant along the patient anatomy based on the visual gradient.

In some embodiments, the imaging device may be configured to capture the at least one image according to a plurality of scan parameters. The plurality of scan parameters may include an exposure time parameter, a voltage parameter and an amperage parameter. The method may include setting, prior to the capturing step, at least one of the scan parameters in response to a previous iteration of the determining step.

In some embodiments, the method may include generating a histogram graph comprising a frequency of the assigned radiodensity values. The method may include comparing a profile of the histogram graph to a predetermined profile. The setting step may occur in response to the comparing the profile.

In some embodiments, the patient anatomy may include a cortical wall surrounding a cancellous region of a bone associated with a joint.

FIGS. 1-4 illustrate an exemplary calibration object 20. The calibration object 20 may be utilized for calibrating images of patient anatomy. The images may be acquired or captured by various imaging devices and/or in various lighting and other conditions.

Referring to FIG. 1, the calibration object 20 may include a main body 22 and one or more density members 24. The density members 24 may establish respective radiodensity regions along the calibration object 20. The density members 24 may be arranged in various configurations. For example, the calibration object 20 may be formed such that the density members 24 are distributed in an array 26 along the main body 22.

Figure 2:
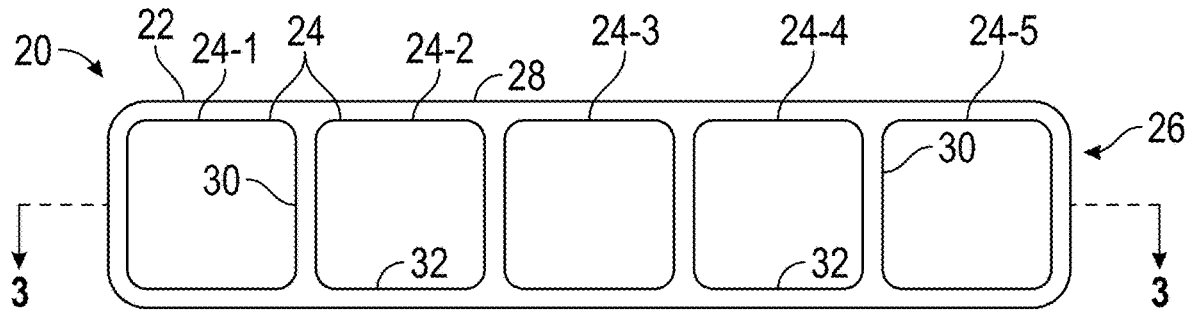
Figure 3:
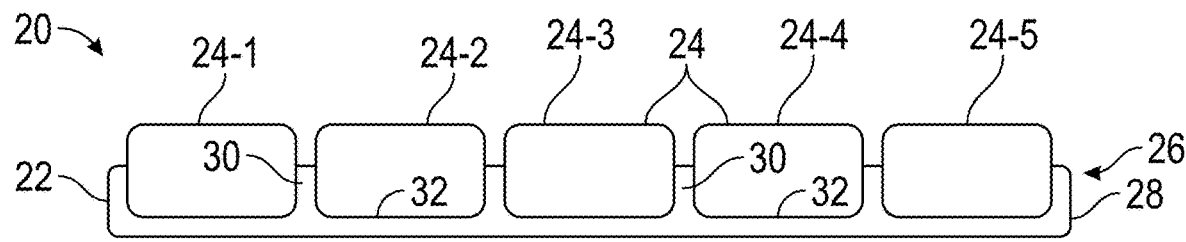

Referring to FIGS. 2-3, with continuing reference to FIG. 1, the main body 22 may include an external wall 28 that may establish a perimeter of the calibration object 20. The external wall 28 may be configured to at least partially or completely surround each of the density members 24, as illustrated in FIG. 2. The main body 22 may include one or more partitions 30. The partitions 30 may be dimensioned to extend or span between opposed sides of the external wall 28 to space apart adjacent pairs of the density members 24.

The calibration object 20 may have various quantities of the density members 24. The calibration object 20 may include three or more density members 24, such as five density members 24 as illustrated in FIGS. 1-3 (indicated at 24-1 to 24-5). It should be understood that fewer or more than five density members 24 may be utilized, such as only one or two density members 24 or more than five density members 24.

Various techniques may be utilized to construct or otherwise form the calibration object 20. In implementations, the main body 22 and density members 24 may be separate and distinct components with one or more of the density members 24 insertable into respective recesses 32 of the main body 22. The main body 22 may be dimensioned to carry each of the density members 24. Each density member 24 may be removable from the respective recess 32 and replaced with another density member 24 that has a different radiodensity than the removed density member 24. Utilizing this technique, the surgeon or operator may reconfigure the calibration object 20 based on the selected imaging device and/or associated conditions in which images of the patient anatomy may be captured or acquired.

Figure 4:
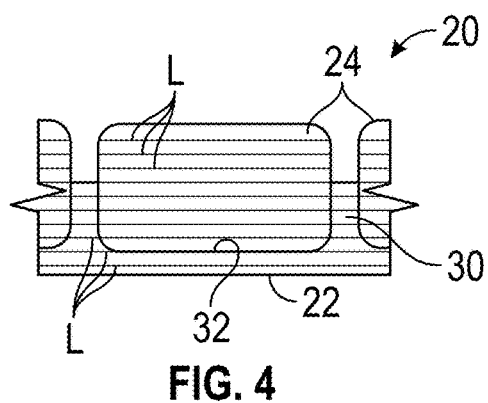
FIG. 4 illustrates layers of a calibration object.

In other implementations, the calibration object 20 may have a monolithic construction. The main body 22 may be formed together with the density members 24 to establish the monolithic construction. The calibration object 20 may be formed by a plurality of layers L which may be contiguous with each other. The layers L may be formed in a stacked relationship to establish at least a portion of the main body 22 and one or more, or each, of the density members 24, as illustrated in FIG. 4. Each layer L may be made of a single material having a substantially uniform radiodensity or may include regions of different materials having substantially the same or different radiodensities, and adjacent layers L may be formed of the same material or different materials to establish the main body 22 and density members 24. Each layer L may be continuous or discontinuous, and may establish regions having substantially the same or different materials, constructions and/or radiodensities establishing the respective layer.

Various techniques may be utilized to form the calibration object 20. Example techniques including injection molding and casting methods. In implementations, the calibration object 20 formed by printing the layers L utilizing three-dimensional (3D) printing techniques. The calibration object 20 may be printed or otherwise formed from a digital file, such as a computer-aided design (CAD) model, by forming one or more successive layers L of material on a substrate. Each digital file may be stored in or associated with one or more records in a database. A 3D printer may include a controller coupled to at least one printing head. The printing head may be coupled to one or more material sources that each may supply a respective amount of material in operation, including any of the materials disclosed herein. The materials supplied by the material sources may be the same or may differ. The controller may command the printing head to form the layers L of material according to the selected digital file to establish the selected calibration object 20.

Materials of the calibration object 20 may be selected for calibrating images of patient anatomy. The materials may be selected such that volumes of the main body 22 and each of the density members 24 correspond to respective radiodensities. For the purposes of this disclosure, the term "radiodensity" means the degree in which a substance or object absorbs electromagnetic radiation, such as an X-ray beam. Objects being less dense and that may generally permit electromagnetic radiation to pass therethrough may be referred to as being relatively "radiolucent," whereas objects being more dense and may generally resist electromagnetic radiation to pass therethrough may be referred to as being relatively "radiopaque." In radiography, portions of an image that appear light may have a relatively high radiodensity, whereas portions of the image that appear dark may have a relatively low radiodensity.

The main body 22 and density members 24 of the calibration object 20 may be formed with various materials having the same and/or different radiodensities. For example, the radiodensity of two or more density members 24 may be the same or may differ from each other and/or the main body 22. Exemplary materials may include organic and naturally occurring materials such as bone tissue and hydroxyapatite. The bone tissue may be de-mineralized cadaver or bovine bone. Other exemplary materials include inorganic materials including thermoplastics and other polymers such as polypropylene (PP), polyvinylidene difluoride (PVDF) and polytetrafluoroethylene (PTFE). Materials of the main body 22 and density members 24 may be selected to establish a resistance to distortion or scatter during image acquisition.

The calibration object 20 may be formed such that the radiodensity of the volume of the main body 22 and the volume of each of the density members 24 correspond to respective predetermined radiodensity values. The predetermined radiodensity values may be expressed in Hounsfield units (HU). The Hounsfield scale is a quantitative scale that may be utilized to quantify the radiodensity of material, with the Hounsfield unit (HU) being a dimensionless unit along the Hounsfield scale. The Hounsfield scale may include HU values within a range of approximately −1024 HU to approximately 3100 HU. Typical tissue types may include a value of approximately −1024 HU which may correspond to air (e.g., lumen of lungs). Values of approximately −120 HU to approximately −75 HU may correspond to apidose tissue. Values of approximately 70 HU to approximately 90 HU may correspond to ligament tissue, such as a ligament of a knee joint. Values of approximately 30 HU to approximately 150 HU may correspond to muscle tissue. Values of approximately 80 HU to approximately 120 HU may correspond to tendon tissue. Values of approximately 300 HU to approximately 500 HU may correspond to trabecular (e.g., cancellous) bone. Values of approximately 500 HU to approximately 1800 HU may correspond to cortical bone. For example, a value of approximately 500 HU to approximately 900 HU may correspond to cortical bone of a humerus or glenoid. Values of approximately 100 HU to approximately 300 HU may correspond to contrast enhanced CT scan images. Various contrast enhancement techniques may be utilized in accordance with the teachings disclosed herein, including intravascular and injected contrast methods. Other techniques may be utilized, including undiluted or Arthrogram contrast techniques, which may be associated with values of approximately 1000 HU or more. The predetermined radiodensity values can be selected to account for application of these and other techniques to the acquired images.

The radiodensity values of the density members 24 may be the same or may differ from each other and/or the main body 22. Each of the density members 24 may have a predetermined radiodensity value that is the same, greater than and/or less than the predetermined radiodensity value of adjacent density member(s) 24.

A volume of each member 24 may have a substantially uniform or non-uniform radiodensity to establish the respective predetermined radiodensity value. In implementations, the density member 24 may be substantially solid and formed of a single material associated with a single radiodensity and/or may have a substantially uniform porosity throughout the volume of the density member 24. In other implementations, the volume of each density member 24 may have a non-uniform radiodensity to establish the respective predetermined radiodensity value. A volume of the density member 24 may comprise materials of different radiodensities or may have a non-uniform porosity forming different regions of the density member 24.

The predetermined radiodensity values of the density members 24 may be within and distributed along a predetermined radiodensity range. The predetermined radiodensity range may extend between a minimum value and a maximum value. The predetermined radiodensity value of the volume of the main body 22 may be less than the minimum value of the predetermined radiodensity range associated with the volumes of the density members 24, which may be utilized to visually distinguish the main body 22 from the density members 24 in the acquired image(s).

Various quantities of the predetermined radiodensity values may be utilized in forming the main body and density members 24 of the calibration object 20. The calibration object 20 may be formed such that the minimum value of the predetermined density range associated with the density members 24 may be greater than or equal to about 0.0 HU, or more narrowly greater than or equal to about 200.0 HU. The maximum value of the predetermined density range may be less than or equal to about 2,000.0 HU. The predetermined radiodensity range may encompass a first radiodensity value of about 300.0 HU and a second radiodensity value of about 1800.0 HU. The minimum value of the predetermined density range may be equal to about 300.0 HU, and the maximum value of the predetermined density range may be equal to about 1800.0 HU. For the purposes of this disclosure, the terms "about," "substantially" and "approximately" mean±5% of the stated value or relationship unless otherwise indicated.

The array 26 of density members 24 may include a first density member 24 and a second density member 24 at opposed ends of the array 26, as illustrated by density members 24-1, 24-5 of FIGS. 2-3. The predetermined radiodensity value of the density member 24-1 may correspond to the minimum value of the predetermined radiodensity range. The predetermined radiodensity value of the density member 24-5 may correspond to the maximum value of the predetermined radiodensity range. In implementations, the calibration object 20 may be formed such that a difference between the radiodensity values of each adjacent pair of the density members 24 may be at least about 5% or about 10% of a difference between the minimum value and the maximum value of the predetermined radiodensity range.

The selected distribution of radiodensities may be utilized to establish a visual contrast in images acquired of patient anatomy, such as X-ray images, computerized tomography (CT) images, magnetic resonance imaging (MRI) images, etc., as discussed in more detail below. The calibration object 20 may be formed with respect to a particular procedure and/or joint, including any of the procedures and joints disclosed herein.

Figure 5:
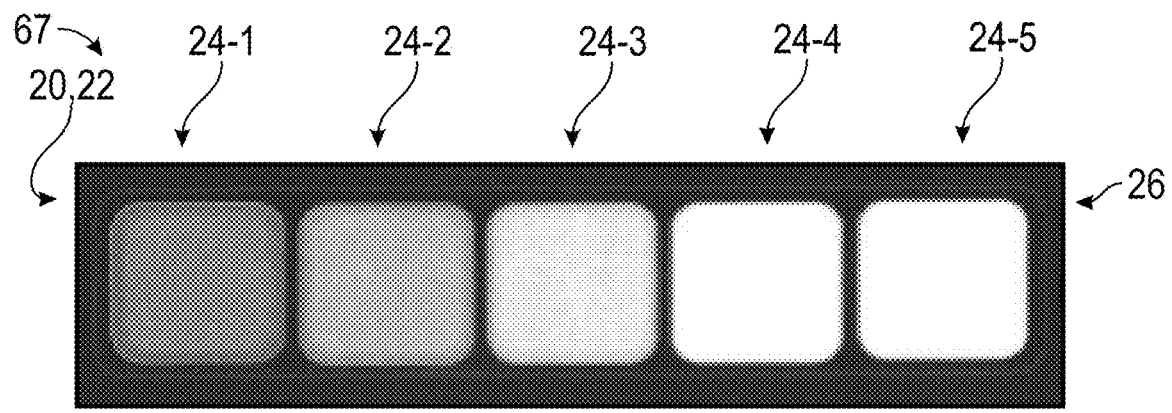
FIGS. 5-6 illustrate images of the calibration object of FIGS. 1-3.
Figure 6:
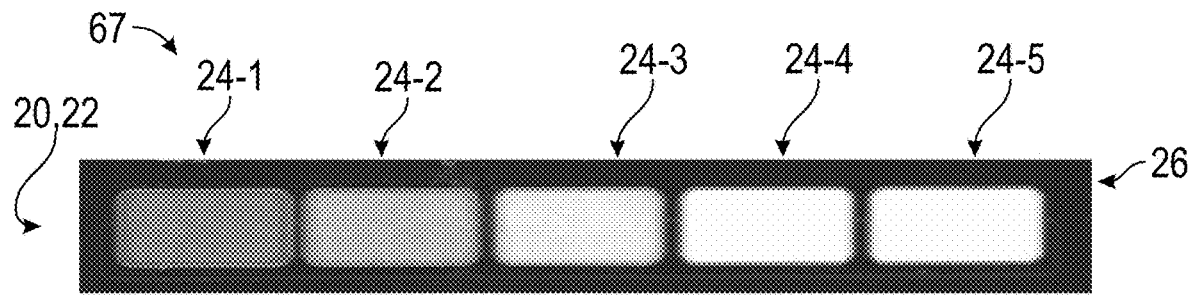

FIGS. 5-6 illustrate the calibration object 20 in an acquired image 67. The acquired image 67 is shown in greyscale for illustrative purposes. The volume of the main body 22 may be substantially radiolucent, as illustrated by the relative dark shading in the acquired image 67. Each of the density members 24 may be formed such that the predetermined radiodensity values of each of the density members 24 is greater than the predetermined radiodensity value of the main body 22.

The calibration object 20 may be formed such that the predetermined radiodensity values of the density members 24-1 to 24-5 progressively increase in the array 26. For example, the predetermined radiodensity value of the density member 24-1 may be relatively greater than the predetermined radiodensity value of the main body 22, as illustrated by the relatively lighter shading of the density member 24-1 in the acquired image 67. The predetermined radiodensity value of the density member 24-5 may be relatively greater than the radiodensity value of the density members 24-1 to 24-4 such that the density member 24-5 is substantially radiopaque, as illustrated by the substantially light shading of the density member 24-5 in the acquired image 67.

The calibration object 20 may be formed such that the predetermined radiodensity range may span between approximately 300 to approximately 1800 HU, which may be generally representative of bone density. The predetermined radiodensity values of the density members 24-1 to 24-5 may correspond to values of about 300 H, 500 HU, 900 HU, 1500 HU and 1800 HU, respectively.

Figure 7:
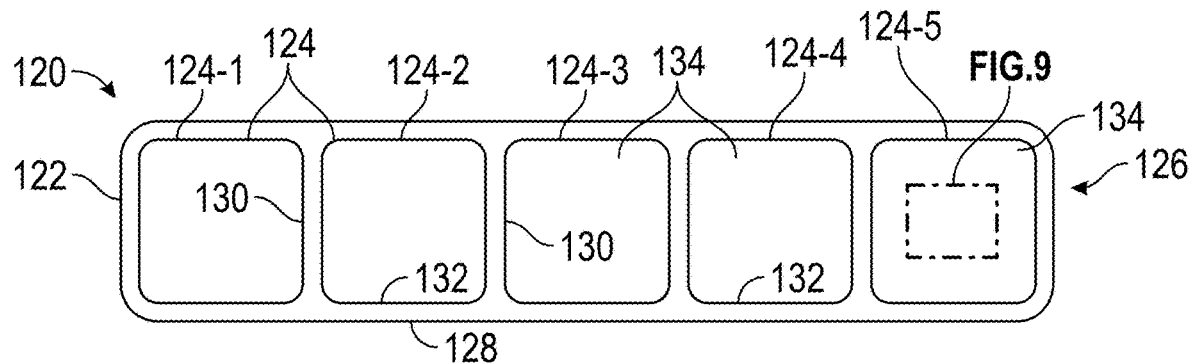
FIGS. 7-9 illustrate another exemplary calibration object.
Figure 8:
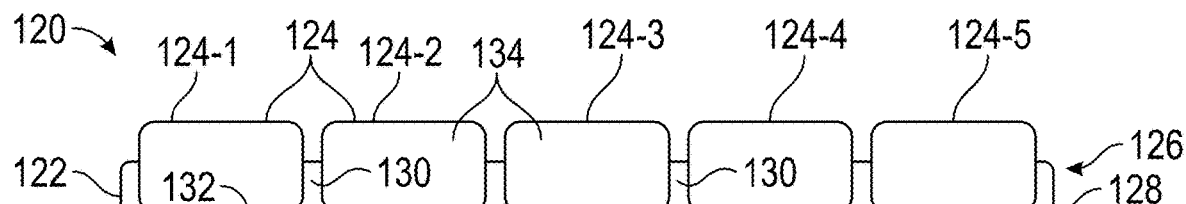
Figure 9:
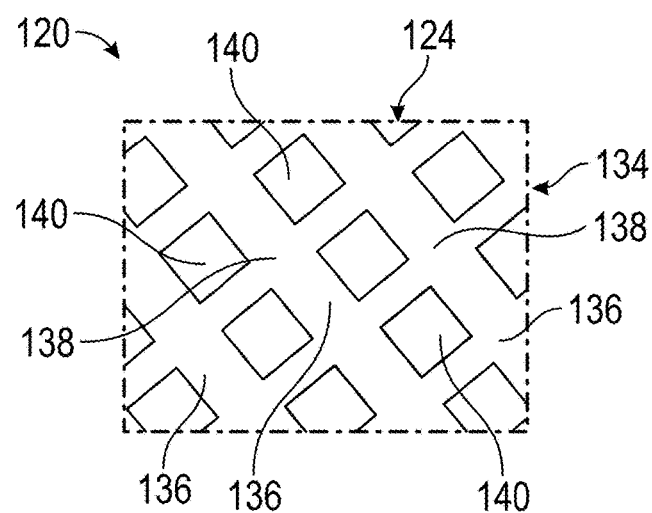

FIGS. 7-9 illustrate another exemplary calibration object 120. In this disclosure, like reference numerals designate like elements where appropriate and reference numerals with the addition of one-hundred or multiples thereof designate modified elements that are understood to incorporate the same features and benefits of the corresponding original elements. The calibration object 120 may include a main body 122 and one or more density members 124. The density members 124 may be distributed in an array 126 along the main body 122. Each of the density members 124 may include a porous scaffold 134 establishing a volume of the respective density member 124.

Referring to FIG. 9, with continuing reference to FIGS. 7-8, the scaffold 134 may include an interconnected network of branches 136 and nodes 138 that may extend through the volume of the respective density member 124. The branches 136 and nodes 138 may be dimensioned to establish one or more voids 140 extending throughout the volume of the density member 124. The scaffold 134, including the branches 136, nodes 138, and/or voids 140, may be dimensioned according to the predetermined density value for the respective density member 124. For example, thicknesses of the branches 136 and nodes 138 and/or volumes of the voids 140 may be varied (e.g., increased or decreased) to establish the respective predetermined density value. The branches 136, nodes 138 and voids 140 may be uniformly or non-uniformly distributed to establish the volume of the density member 124. The density members 124 may be formed utilizing any of the techniques disclosed herein, including any of the disclosed radiodensity values, materials and arrangements.

Figure 10:
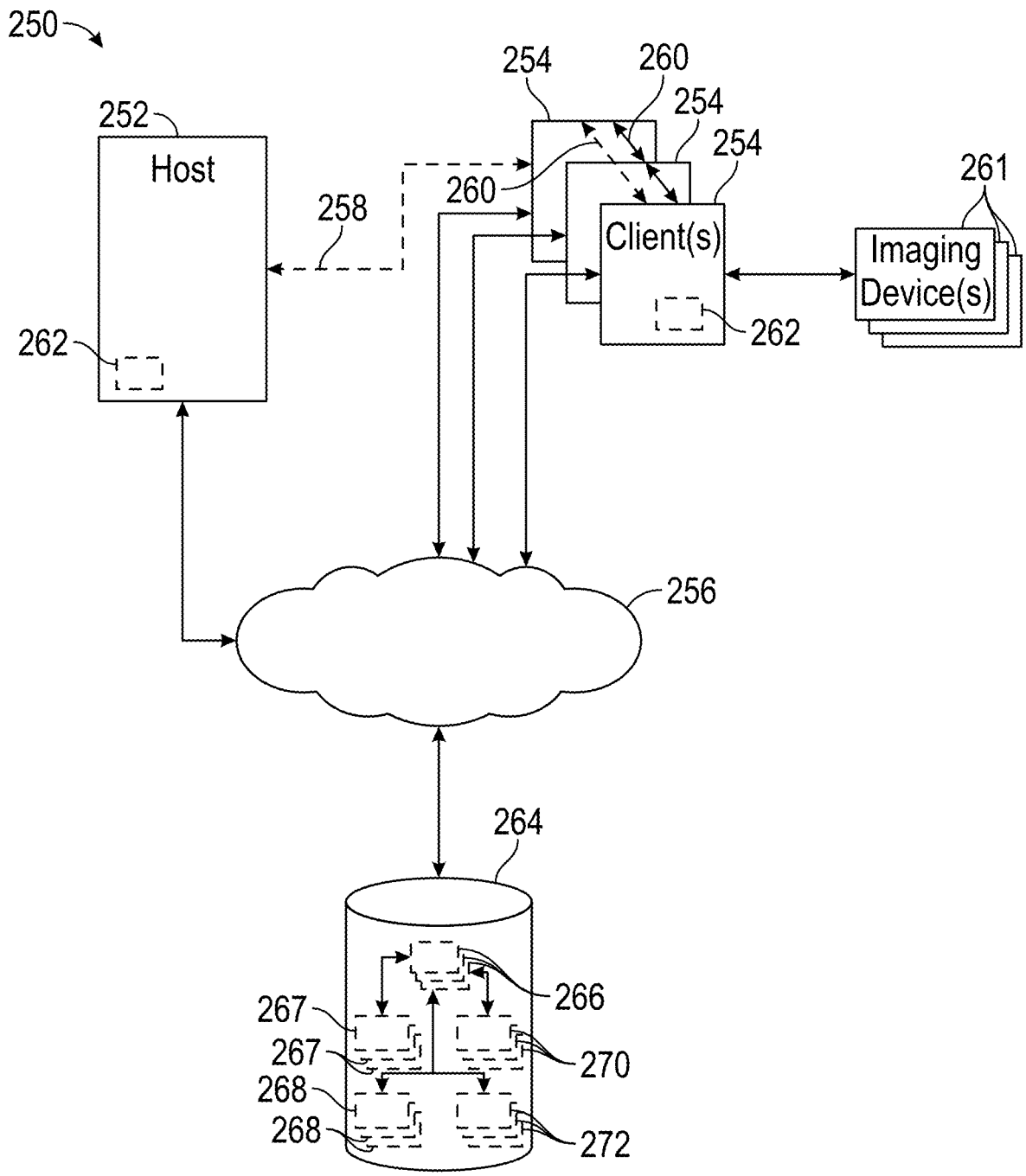
FIG. 10-12 illustrates an exemplary planning system including a user interface.

FIG. 10 illustrates an exemplary planning (e.g., imaging) system 250 that may be utilized for planning surgical procedures. The system 250 may be used for planning orthopaedic procedures, including pre-operatively, intra-operatively and/or post-operatively to create, edit, execute and/or review surgical plans. The system 250 may be utilized for various orthopaedic and other surgical procedures, such as an arthroplasty to repair a joint. The system 250 may be utilized in the placement of an implant, such as an implant incorporated into a shoulder prosthesis, for example. Although the planning systems and methods disclosed herein primarily refer to repair of a glenoid or humerus during an anatomic or reverse shoulder reconstruction, it should be understood that the planning system 250 may be utilized in the repair of other locations of the patient and other surgical procedures including repair of a glenoid and other joints such as a wrist, hand, hip, knee or ankle, and including repair of fractures.

The system 250 may include a host computer 252 and one or more client computers 254. The host computer 252 may be configured to execute one or more software programs. In some implementations, the host computer 252 is more than one computer jointly configured to process software instructions serially or in parallel.

The host computer 252 may be in communication with one or more networks such as a network 256 comprised of one or more computing devices. The network 256 may be a private local area network (LAN), a private wide area network (WAN), the Internet, or a mesh network, for example.

The host computer 252 and each client computer 254 may include one or more of a computer processor, memory, storage means, network device and input and/or output devices and/or interfaces. The input devices may include a keyboard, mouse, etc. The output device may include a monitor, speakers, printers, etc. The memory may, for example, include UVPROM, EEPROM, FLASH, RAM, ROM, DVD, CD, a hard drive, or other computer readable medium which may store data and/or other information relating to the planning and calibration techniques disclosed herein. The host computer 252 and each client computer 254 may be a desktop computer, laptop computer, smart phone, tablet, or any other computing device. The interface may facilitate communication with the other systems and/or components of the network 256.

Each client computer 254 may be configured to communicate with the host computer 252 directly via a direct client interface 258 or over the network 256. In another implementation, the client computers 254 are configured to communicate with each other directly via a peer-to-peer interface 260.

The system 250 may include, or may be coupled to, one or more imaging devices 261. Each client computer 254 may be coupled to one or more imaging devices 261, for example. Each imaging device 261 may be configured to capture or acquire one or more images 267 of patient anatomy residing within a scan field (e.g., window) of the imaging device 261. The imaging device 261 may be configured to capture or acquire two dimensional (2D) and/or three dimensional (3D) greyscale and/or color images 267. Various imaging devices 261 may be utilized, such as an X-ray machine, computerized tomography (CT) machine or magnetic resonance imaging (MRI) machine that obtains one or more images of a patient. The imaging device 261 may be configured to capture images 267 according to one or more scan parameters. Exemplary scan parameters may include an exposure time parameter, a voltage parameter and an amperage parameter.

The client computers 254 may be configured to execute one or more software programs, such as a various surgical tools. Each client computer 254 may be operable to access and locally and/or remotely execute a planning environment 262. The planning environment 262 may be a standalone software package or may be incorporated into another surgical tool. The planning environment 262 may be configured to communicate with the host computer 252 either over the network 256 or directly through the direct client interface 258.

The planning environment 262 may be configured to interact with one or more of the imaging devices 261 to capture or acquire images 267 of patient anatomy. The planning environment 262 may provide a display or visualization of one or more images 267, bone models 268 and/or implant models 270 via one or more graphical user interfaces (GUI). Each image 267, bone model 268, implant model 270 and other data and information may be stored in one or more files or records according to a specified data structure.

The system 250 may include at least one storage system 264, which may be operable to store or otherwise provide data to other computing devices. The storage system 264 may be a storage area network device (SAN) configured to communicate with the host computer 252 and/or the client computers 254 over the network 256. In implementations, the storage system 264 may be incorporated within or directly coupled to the host computer 252 and/or client computers 254. The storage system 264 may be configured to store one or more of computer software instructions, data, database files, configuration information, etc.

In some implementations, the system 250 may be a client-server architecture configured to execute computer software on the host computer 252, which may be accessible by the client computers 254 using either a thin client application or a web browser executing on the client computers 254. The host computer 252 may load the computer software instructions from local storage, or from the storage system 264, into memory and may execute the computer software using the one or more computer processors.

The system 250 may include one or more databases 266. The databases 266 may be stored at a central location, such as the storage system 264. In another implementation, one or more databases 266 may be stored at the host computer 252 and/or may be a distributed database provided by one or more of the client computers 254. Each database 266 may be a relational database configured to associate one or more images 267, bone models 268 and/or implant models 270 to each other and/or a surgical plan 272. Each surgical plan 272 may be associated with a respective patient. Each image 267, bone model 268, implant model 270 and surgical plan 272 may be assigned a unique identifier or database entry. The database 266 may be configured to store data and other information corresponding to the images 267, bone models 268, implant models 270 and surgical plans 272 in one or more database records or entries, and/or may be configured to link or otherwise associate one or more files corresponding to each respective image 267, bone model 268, implant model 270 and surgical plan 272. Images 267 and bone models 268 stored in the database(s) 266 may correspond to respective patient anatomies from prior surgical cases, and may be arranged into one or more predefined categories such as sex, age, ethnicity, defect category, procedure type, etc.

Each image 267 and bone model 268 may include data and other information obtained from one or more medical devices or tools, such as the imaging devices 261. The bone model 268 may include coordinate information relating to an anatomy of the patient obtained or derived from images 267 captured or otherwise obtained by the imaging device(s) 261. Each implant model 270 may include coordinate information associated with a predefined design. The planning environment 262 may incorporate and/or interface with one or more modeling packages, such as a computer aided design (CAD) package, to render the models 268, 270 as two-dimensional (2D) and/or three-dimensional (3D) volumes or constructs, which may overlay one or more of the images 267 in a display screen of a GUI.

The implant models 270 may correspond to implants and components of various shapes and sizes. Each implant may include one or more components that may be situated at a surgical site including screws, anchors and/or grafts. Each implant model 270 may correspond to a single component or may include two or more components that may be configured to establish an assembly. Each implant and associated component(s) may be formed of various materials, including metallic and/or non-metallic materials. Each bone model 268 and implant model 270 may correspond to 2D and/or 3D geometry, and may be utilized to generate a wireframe, mesh and/or solid construct in a display.

Each surgical plan 272 may be associated with one or more of the images 267, bone models 268 and implant models 270. The surgical plan 272 may include various parameters associated with the images 267, bone models 268 and/or implant models 270. For example, the surgical plan 272 may include parameters relating to bone density and bone quality associated with patient anatomy captured in the images 267.

The surgical plan 272 may include one or more revisions to a bone model 268 and information relating to a position of an implant model 270 relative to the original and/or revised bone model 268. The surgical plan 272 may include coordinate information relating to the revised bone model 268 and a relative position of the implant model 270 in predefined data structure(s). Revisions to each bone model 268 and surgical plan 272 may be stored in the database 266 automatically and/or in response to user interaction with the system 250.

One or more surgeons and other users may be provided with a planning environment 262 via the client computers 254 and may simultaneously access each image 267, bone model 268, implant model 270 and surgical plan 272 stored in the database(s) 266. Each user may interact with the planning environment 262 to create, view and/or modify various aspects of the surgical plan 272. Each client computer 254 may be configured to store local instances of the images 267, bone models 268, implant models 270 and/or surgical plans 272, which may be synchronized in real-time or periodically with the database(s) 266. The planning environment 262 may be a standalone software package executed on a client computer 254 or may be provided as one or more services executed on the host computer 252, for example.

Figure 11:
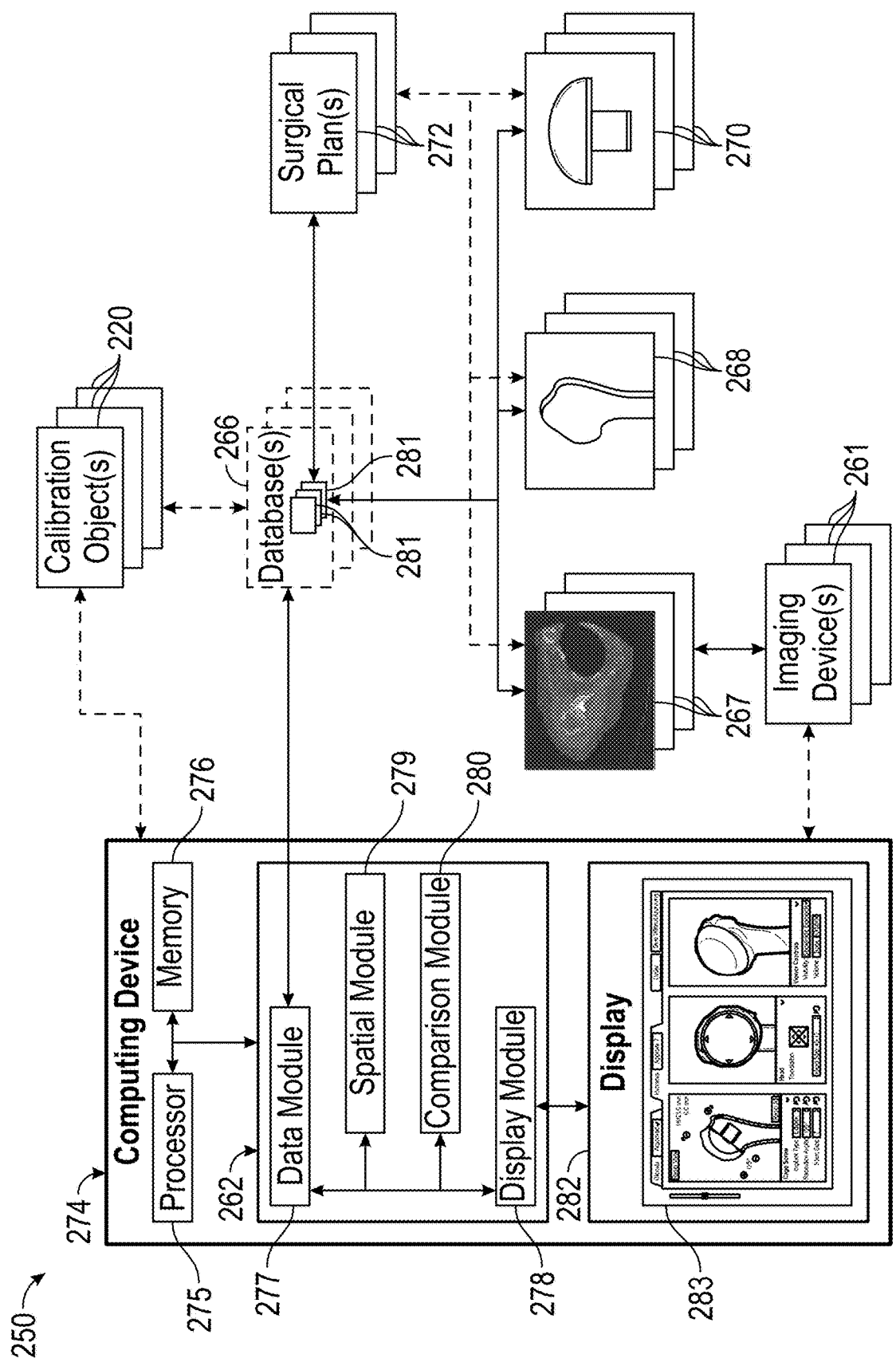

Referring to FIG. 11, with continuing reference to FIG. 10, the system 250 may include a computing device 274 including at least one processor 275 coupled to memory 276. The computing device 274 may include any of the computing devices disclosed herein, including the host computer 252 and/or client computer 254. The processor 275 may be configured to execute a planning environment 262 for capturing, acquiring, retrieving, storing, editing and/or calibrating one or more images 267 of patient anatomy. The images 267 may be captured or acquired from the imaging device(s) 261 and/or may be obtained from one or more external sources. The images 267 may include any of the image types disclosed herein, including X-ray images, CT images and MRI images, which may be captured or acquired by any of the imaging devices disclosed herein. The processor 275 may be configured to execute the planning environment 262 for creating, editing, executing and/or reviewing one or more surgical plans 272 during pre-operative, intra-operative and/or post-operative phases of a surgery.

The planning environment 262 may include at least a data module 277, a display module 278, a spatial module 279 and a comparison module 280. Although four modules are shown, it should be understood that fewer or more than four modules may be utilized and/or one or more of the modules may be combined to provide the disclosed functionality.

The data module 277 may be configured to access, retrieve and/or store data and other information in the database(s) 266 corresponding to one or more images 267 of patient anatomy, bone model(s) 268, implant model(s) 270 and/or surgical plan(s) 272. The data and other information may be stored in one or more databases 266 as one or more records or entries 281. In some implementations, the data and other information may be stored in one or more files that are accessible by referencing one or more objects or memory locations referenced by the records 281.

The memory 276 may be configured to access, load, edit and/or store instances of one or more images 267, bone models 268, implant models 270 and/or surgical plans 272 in response to one or more commands from the data module 277. The data module 277 may be configured to cause the memory 276 to store a local instance of the image(s) 267, bone model(s) 268, implant model(s) 270 and/or surgical plan(s) 272, which may be synchronized with the records 281 in the database(s) 266.

The data module 277 may be configured to receive data and other information corresponding to at least one or more images 267 of patient anatomy together with one or more calibration objects 220 from various sources such as the imaging device(s) 261. The data module 277 may be configured to command the imaging device 261 to capture or acquire the images 267 automatically or in response to user interaction.

The display module 278 may be configured to display data and other information relating to one or more surgical plans 272 in at least one graphical user interface (GUI) 283, including one or more of the images 267. The computing device 274 may incorporate or be coupled to a display device 282. The display module 278 may be configured to cause the display device 282 to display information in the user interface 283. A surgeon or other user may interact with the user interface 283 via the planning environment 262 to view one or more images 267, alone and/or together with the calibration object(s) 220. The surgeon or other user may interact with the user interface 283 via the planning environment 262 to create, edit, execute and/or review one or more surgical plans 272.

Figure 12:
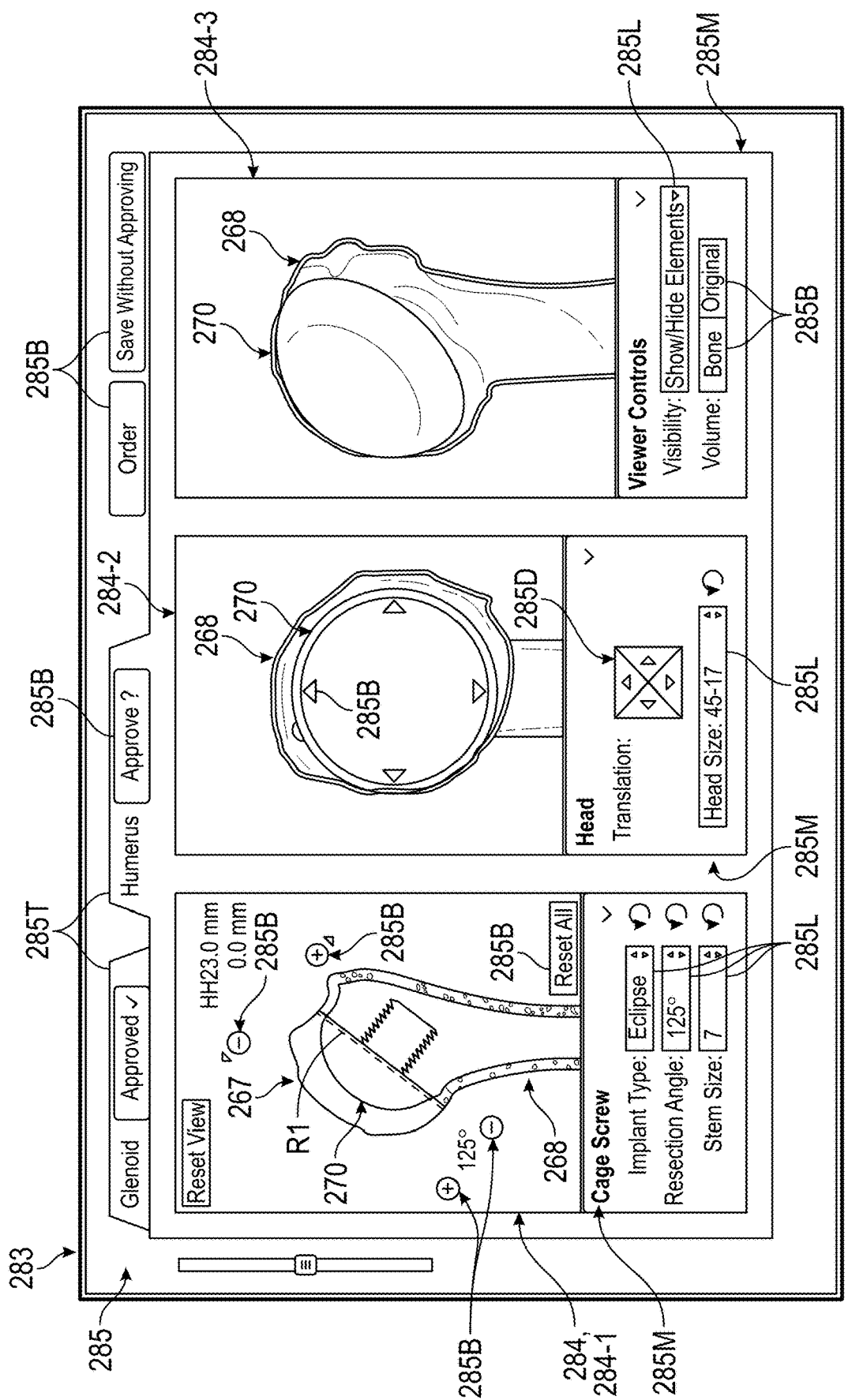

Referring to FIG. 12, with continuing reference to FIG. 11, the user interface 283 may include one or more display windows 284 and one or more objects 285. The display windows 284 may include first, second and third display windows 284-1, 284-2, 284-3. Although three display windows 284 are shown, it should be understood that fewer or more than three display windows 284 may be utilized in accordance with the teachings disclosed herein.

A surgeon or user may interact with the user interface 283 including the objects 285 and/or display windows 284 to retrieve, view, edit, store, etc., various aspects of a surgical plan 272, such as the selected image(s) 267, bone model(s) 268 and/or implant model(s) 270. The objects 285 may include graphics such as menus, tabs and buttons accessible by user interaction, such as tabs 285T, buttons 285B, drop-down lists 285L, and directional indicator 285D. The objects 285 may be organized in one or more menu items 285M associated with the respective display windows 284. Geometric objects including selected image(s) 267, bone model(s) 268, implant model(s) 270 and/or other information relating to the surgical plan 272 may be displayed in one or more of the display windows 284.

The surgeon may interact with the objects 285 to specify various aspects of a surgical plan 272. For example, the surgeon may select one of the tabs 285T to view or specify aspects of the surgical plan 272 for one portion of a joint, such as a glenoid, and may select another one of the tabs 285T to view or specify aspects of the surgical plan 272 for another portion of the joint, such as a humerus.

The surgeon may interact with the menu items 285M to select and specify various aspects of the image 267, bone model 268 and/or implant model 270 from the database 266. For example, the display module 278 may be configured to display one or more bone models 268 together with the respective image(s) 267 of the patient anatomy selected in response to user interaction with the user interface 283. The user may interact with the drop-down lists 285L associated with the first display window 284-1 to specify implant type, resection angle and implant size. The resection angle menu item may be associated with a resection plane R1 (shown in dashed lines in window 284-1 for illustrative purposes).

The user may interact with buttons 285B to change (e.g., increase or decrease) the resection angle. The user may interact with buttons 285B adjacent the selected implant model 270 to change (e.g., increase or decrease) a size of a component of the selected implant model 270. The buttons 285B may be overlaid onto or may be situated adjacent to the display windows 284. The user may interact with the directional indicator 285D to move a portion of the selected implant model 270 in different directions (e.g., up, down, left, right) in the second display window 284-2. The surgeon may drag or otherwise move the selected implant model 270 to a desired position in the second display window 284-2 utilizing a mouse, for example. The surgeon may interact with one of the drop-down lists 285L to specify a type and/or size of a component of the selected implant model 270.

The display module 278 may be configured to superimpose one or more of the bone models 268 and/or implant models 270 over one or more of the images 267, as illustrated by window 284-1. The implant model 270 may include one or more components that establish an assembly. At least a portion of the implant model 270 may be configured to be at least partially received in a volume of a selected one of the bone models 268. The implant model 270 may have an articulation surface dimensioned to mate with an articular surface of an opposed bone or implant.

The display windows 284 may be configured to display the images 267, bone models 268 and/or implant models 270 at various orientations. The display module 278 may be configured to display two dimensional (2D) representation(s) of the selected bone model(s) 268 and/or implant model(s) 270 in the first and/or second display windows 284-1, 284-2, and may be configured to display 3D representation(s) of the selected bone model 268 and/or implant model 270 in the third display window 284-3, for example. The surgeon may interact with the user interface 283 to move the selected bone model 268 and/or selected implant model 270 in 2D space (e.g., up, down, left, right) and/or 3D space. In other implementations, the display module 278 may be configured to display a 2D representation of the selected bone model 268 and/or selected implant model 270 in the third display window 284-3.

The display module 278 may be configured such that the selected image(s) 267, bone model(s) 268 and/or implant models 270 may be selectively displayed and hidden (e.g., toggled) in one or more of the display windows 284 in response to user interaction with the user interface 283, which may provide the surgeon with enhanced flexibility in reviewing aspects of the surgical plan 272. For example, the surgeon may interact with the drop-down lists 285L to selectively display and hide components of the selected implant model 270 in the third display window 284-3.

The selected bone model 268 may correspond to a bone associated with a joint, including any of the exemplary joints disclosed herein, such as a humerus as illustrated in FIG. 12. The display module 278 may be configured to display a sectional view of the selected bone model 268 and/or selected implant model 270 in the first viewing window 284-1, for example. The sectional view of the bone model(s) 268 may be presented or displayed together with the associated image(s) 267 of the patient anatomy.

The spatial module 279 may be configured to establish the resection plane R1 along the selected bone model 268. A volume of the selected implant model 270 may be at least partially received in a volume of the selected bone model 268 along the resection plane R1. The resection plane R1 may be defined by a resection angle.

The spatial module 279 may be configured to cause the display module 278 to display an excised portion of the selected bone model 268 to be displayed in the first display window 284-1 in a different manner than a remainder of the bone model 268 on an opposed side of the resection plane R1. For example, the excised portion of the bone model 268 may be hidden from display in the first display window 284-1 such that the respective portion of the image 267 of the patient anatomy is shown, as illustrated in FIG. 12. In other implementations, the excised portion of the selected bone model 268 may be displayed in a relatively darker shade. The spatial module 279 may determine the excised portion by comparing coordinates of the bone model 268 with respect to a position of the resection plane R1, for example. The user may interact with one or more buttons 285B to toggle between a volume of previous and revised (e.g., resected) states of the selected bone model 268.

The planning environment 262 may be configured such that changes in one of the display windows 284 are synchronized with each of the other windows 284. The changes may be synchronized between the display windows 284 automatically and/or manually in response to user interaction.

Figure 13:
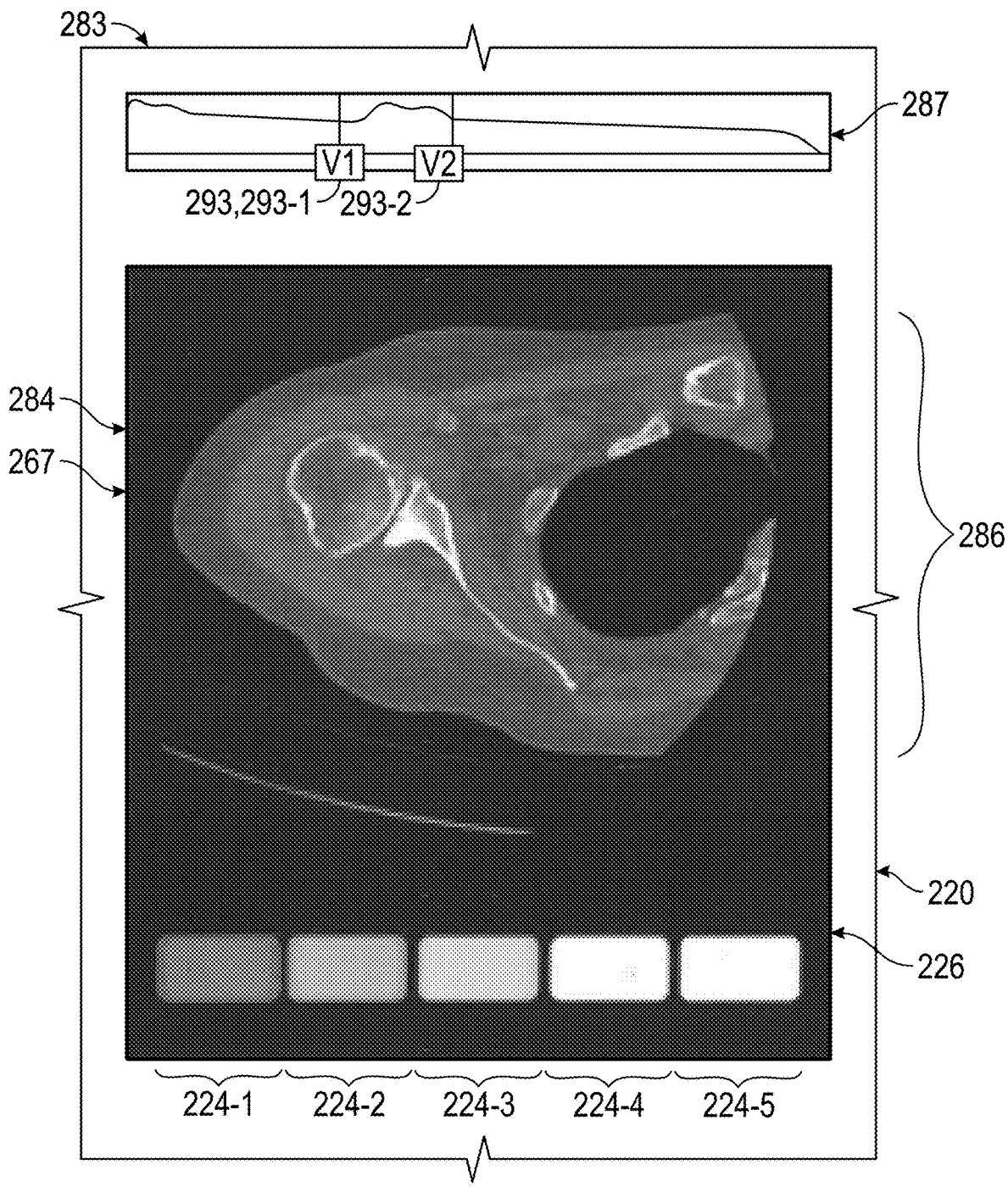
FIG. 13-19 illustrate images relating to patient anatomy.

Referring to FIG. 13, with continuing reference to FIGS. 11-12, the data module 277 may be configured to receive data corresponding to one or more images 267 of patient anatomy 286 together with the calibration object(s) 220 from the imaging device(s) 261. The surgeon may interact with the user interface 283 to view and evaluate selected image(s) 267 from various sources including images 267 of patient anatomy 286 captured or acquired by the imaging devices 261, such as portions of a shoulder joint including a glenoid and humerus as illustrated in FIG. 13. The calibration object 220 may be displayed in the image 267 adjacent the patient anatomy 286. The image 267 is shown in greyscale for illustrative purposes.

The calibration object 220 includes an array 226 of density members 224 (indicated at 224-1 to 224-5) displayed in the image 267. The density members 224 may be formed utilizing any of the techniques disclosed herein. The density members 224 may include any of the radiodensities and associated predetermined radiodensity values disclosed herein.

Portions of the image 267 associated with the calibration object 220 and/or patient anatomy 286 having relatively lower radiodensities are illustrated in relatively dark shading. Portions of the image 267 associated with the calibration object 220 and/or patient anatomy 286 having relatively higher radiodensities are illustrated in relatively lighter shading, such as cortical bone of the glenoid and humerus. Portions of the image 267 having an intermediate (e.g., grey) shading may correspond to cancellous bone surrounded by the cortical bone. Cortical bone may comprise substantially hard and dense bone tissue, whereas cancellous bone may comprise relatively porous, spongy bone tissue. The cortical bone may establish a cortical wall that surrounds the cancellous bone.

Figure 14:
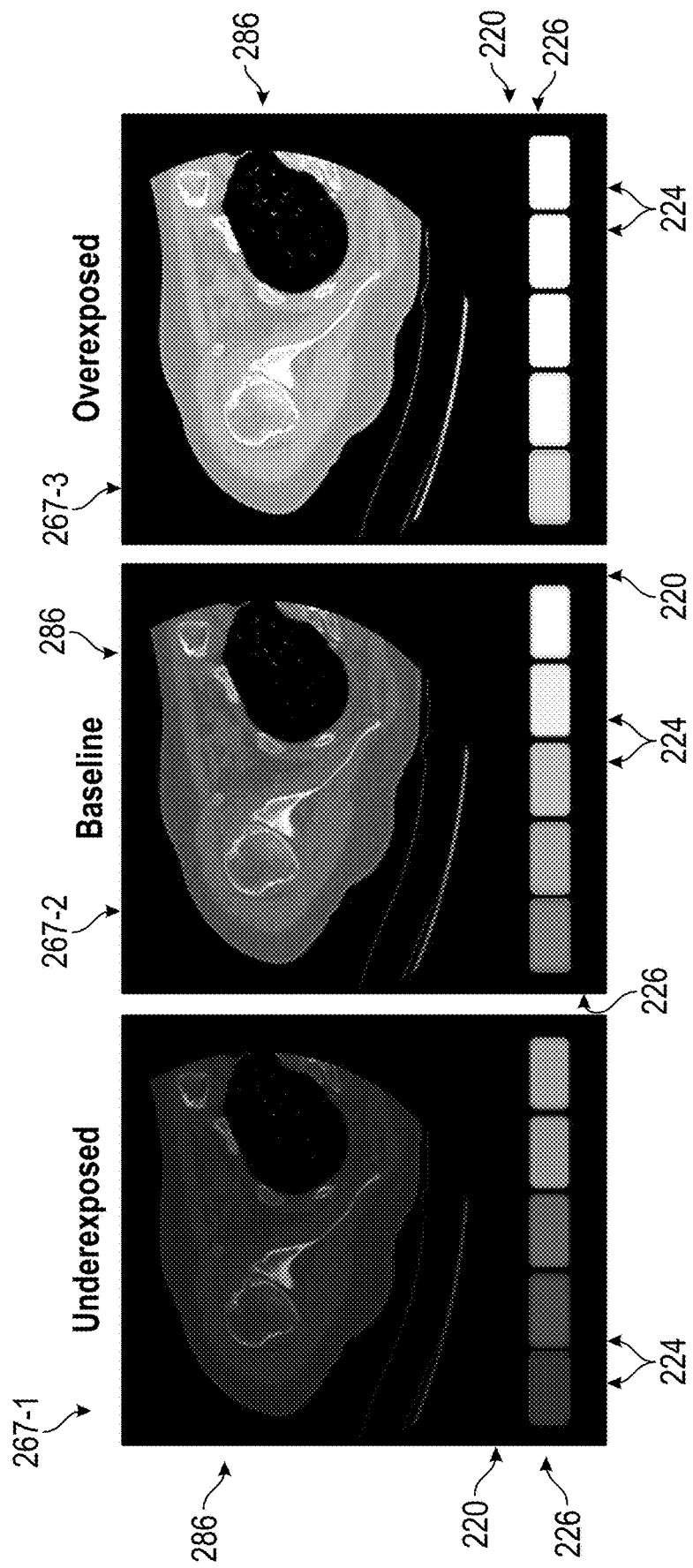

The pixel values of the image 267 may vary depending on characteristics of the imaging device 261 and various conditions associated with capturing the image 267, including the various scan parameters of the imaging device 261 and an environment in which the images 267 are captured such as lighting and other conditions. The scan parameter may include any of the parameters disclosed herein, including an exposure time parameter, a voltage parameter and an amperage parameter. FIG. 14 illustrates an underexposed image 267-1, a baseline (e.g., normal) image 267-2, and an overexposed image 267-3. The patient anatomy 286 and calibration object 220 in the underexposed and overexposed images 267-1, 267-3 may have relatively lesser contrast than in the baseline image 267-2. Variation in the conditions during acquisition of the images 267 may reduce the ability to sufficiently determine or infer various aspects of the patient anatomy 286, such as bone density and bone quality of the cancellous and/or cortical bone.

The calibration object 220 may be utilized to calibrate or normalize data and other information in the respective images 267 based on predetermined radiodensity values associated with the density members 224. Each calibration object 220 may be associated with a respective profile assigned a unique identifier associated with the respective predetermined radiodensity values. Different calibration blocks 220 having density members 224 of various predetermined radiodensity values and ranges may be formed for various surgical procedures, joints, imaging devices, conditions, etc. The profile and various parameters of each calibration object 220 may be stored as one or more records 281 in the database(s) 226 (FIG. 11). The profiles associated with the calibration blocks 220 may be selected by the surgeon or other user from the database 266 in response to user interaction with the user interface 283 or may be selected automatically by the system 250 to calibrate the respective images 267.

The planning environment 262 may be configured to include and/or exclude one or more of the density members 224 from image calibration. The display module 278 may be configured to cause the comparison module 280 to include or exclude one or more of the density members 224 from image calibration in response to one or more commands such as user interaction with the user interface 283. The surgeon may interact with the user interface 283 to select a subset of the density members 224 to be utilized in calibrating the acquired images 267. For example, the surgeon may select one or more of the density members 224 in the display windows 284 to be utilized in the calibration and/or may select one or more of the density members 224 to exclude from the calibration. Selection may be made based on a particular surgical procedure or patient anatomy associated with the surgical plan 272, for example.

The comparison module 280 may be configured to determine pixel values for each position in the respective images 267. For example, greyscale images may comprise a range of possible pixel values from 0 to 255. A pixel value of 0 may be associated with black, and a pixel value of 255 may be associated with white. Each position in the image 267 may be associated with a respective pixel value, including positions along the patient anatomy and density members 224 of the calibration object(s) 220 in the scan field of the imaging device 261.

The comparison module 280 may be configured to determine one or more image gradients. Each of the image gradients may be based on a comparison of a pixel value at a respective position in the image 267 and pixel values associated with one or more respective positions along the density members 224 in the image 267. The comparison module 280 may be configured to determine an image gradient for each position in the image 267 and/or a subset of the positions in the image 267 including the patient anatomy 286.

The comparison module 280 may be configured to assign a radiodensity value to one or more positions in the image 267 based upon a comparison of the respective image gradient and predetermined radiodensity value(s) of the density member(s) 224. For example, one of the density members 224 may be associated with a pixel value of 200 and a position along the patient anatomy 286 may be associated with a pixel value of 180. The position along the patient anatomy 286 may be assigned the respective radiodensity value based on a percentage of the difference between the pixel values (e.g., 10%). The comparison module 280 may be configured to assign the radiodensity value based on a single image gradient associated with one of the density members 224, or two or more image gradients associated with two or more (or each) of the density members 224. Comparing the pixel value at each position in the image 267 to the pixel values of two or more of the density members 224 may improve accuracy in determining or estimating an absolute value of the radiodensity at the respective position in the image 267 including along the patient anatomy 286. In implementations, the assigned density value of each position in the image 267 may be based on an average of individual assigned density values calculated with respect to two or more (or each) of the density members 224 of the calibration object 220. An average of the individual assigned density values may be weighted. For example, density members 224 having pixel values closer to the pixel value of a given position may be assigned a relatively greater weight than other density members 224.

The comparison module 280 may cause the data module 277 to obtain the predetermined radiodensity values of the respective density members 224 from the database(s) 266 in assigning the radiodensity values to each of the positions in the image 267. In implementations, various techniques such as machine learning may be utilized to rapidly detect relatively small differences in radiodensity values associated with a set of images 267, which may facilitate a relatively more definitive and standardized comparison of tissue densities.

The display module 278 may be configured to display a histogram graph 287 in the user interface 283. The histogram graph 287 may comprise a frequency of the assigned radiodensity values corresponding to each of the positions in the image 267, or at least a subset of the positions in the image 267 corresponding to the patient anatomy 286 as illustrated in FIG. 13.

Figure 15:
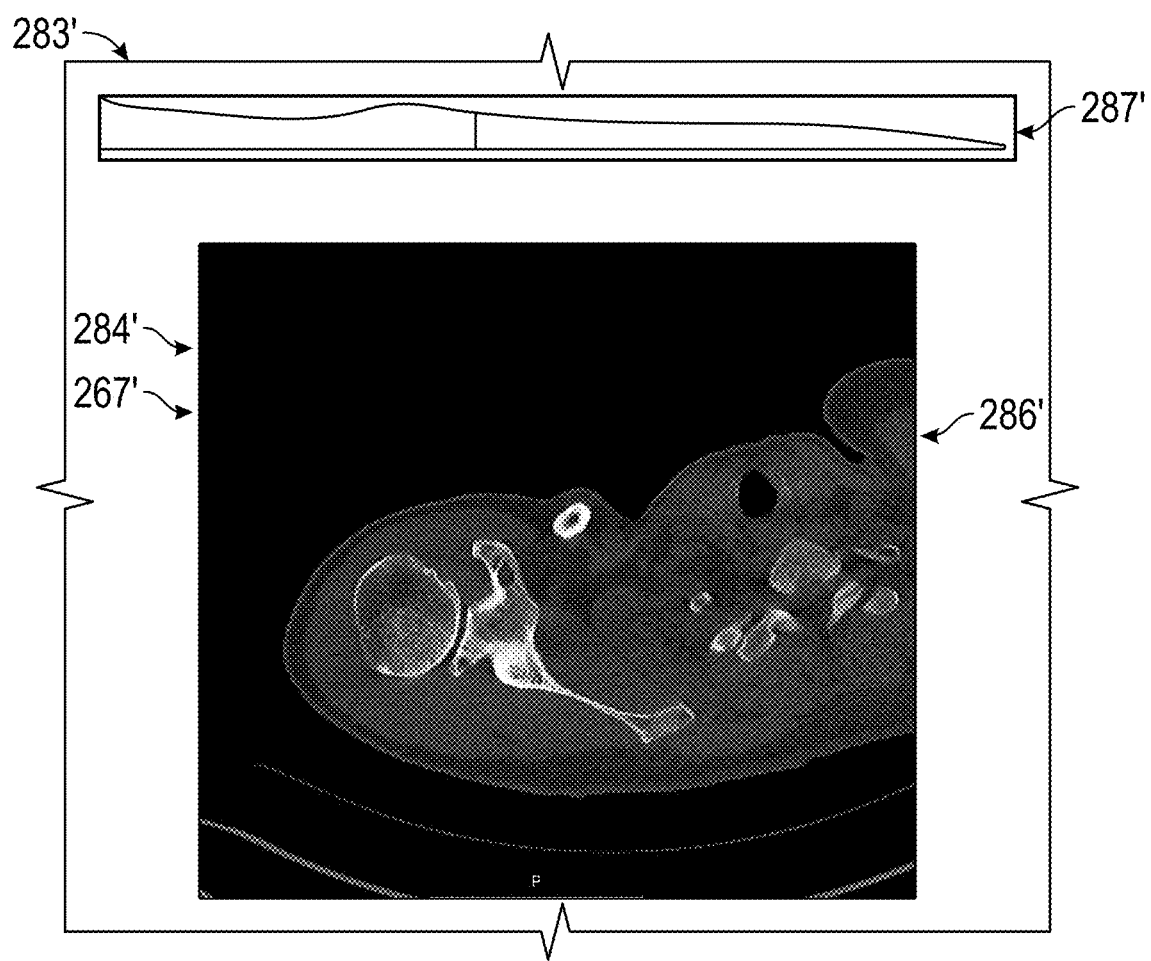

FIG. 15 illustrates another exemplary histogram graph 287' associated with a respective image 267'. The calibration object 220 is omitted for illustrative purposes. The histogram graph 287' is illustrated as having a relatively less pronounced profile at various locations along the graph 287' than a profile of the histogram graph 287 of FIG. 13. For example, the histogram graph 287 may have a relatively more defined mid-range peak than the histogram graph 287' as illustrated by FIGS. 13 and 15.

The comparison module 280 may be configured to cause one or more of the scan parameters of the imaging device(s) 261 to be adjusted prior to capturing or acquiring one or more subsequent image(s) 267 with the imaging device(s) 261 according to the adjusted scan parameter(s). Various techniques may be utilized to determine adjusted scan parameters, such as comparing the profile of the histogram graph 287 to one or more predetermined profiles, and/or comparing a difference between the pixel values associated with two or more of the density members 224 to one or more predetermined thresholds. Predetermined thresholds may include a predetermined underexposure threshold and/or predetermined overexposure threshold established for underexposure and overexposure conditions (see, e.g., FIG. 14). The display module 278 may be configured to display the adjusted scan parameters in the user interface 283, which may be selected or approved by the surgeon, or the adjusted scan parameters may be automatically selected for reconfiguration of the imaging device 261 and subsequent image acquisition.

The comparison module 280 may be configured to cause the display module 278 to display a calibrated instance of the selected image(s) 267. For example, images 267-1, 267-2 of FIG. 14 may be uncalibrated images, and image 267-2 may be a calibrated instance of one of the images 267-1, 267-2. The comparison module 280 may be configured to adjust the pixel values of one or more, or each of, the positions in the uncalibrated images 267-1, 267-2 based on the comparison of the assigned and predetermined density values to generate the calibrated image 267-2. The calibrated image may be displayed in greyscale as illustrated in FIG. 14 or may be color mapped to a predetermined range of colors, for example.

In implementations, the range of pixel values for a given image type are mapped to a predetermined range of radiodensity values, including any of the ranges disclosed herein. Each predetermined range of radiodensity values may be stored as a record 281 in the database 266, which may be accessed by the data module 277. The comparison module 280 may be configured to remap the assigned radiodensity values according to respective values in the predetermined range of radiodensity values, such as assigned radiodensity values for a greyscale image type having permissible pixel values between 0 and 255. The predetermined range of radiodensity values may encompass at least some or all of the predetermined radiodensity values of the density members 224. An assigned radiodensity value at a lower boundary of the predetermined range of radiodensity values may be remapped to a calibrated pixel value of 0, an assigned radiodensity value at an upper boundary of the predetermined range of radiodensity values may be remapped to a calibrated pixel value of 255, and interim assigned radiodensity values may be remapped to interim calibrated pixel values based on a location (e.g., percentage or difference) of the interim assigned radiodensity values with respect to the upper and/or lower boundaries, for example. Each position in the image 267 may be remapped to the predetermined range of radiodensity values to establish a calibrated image 267 that may be displayed in a display window 284 of the user interface 283, such as the image 267 in the display window 284-1 of FIG. 12.

Figure 16A:
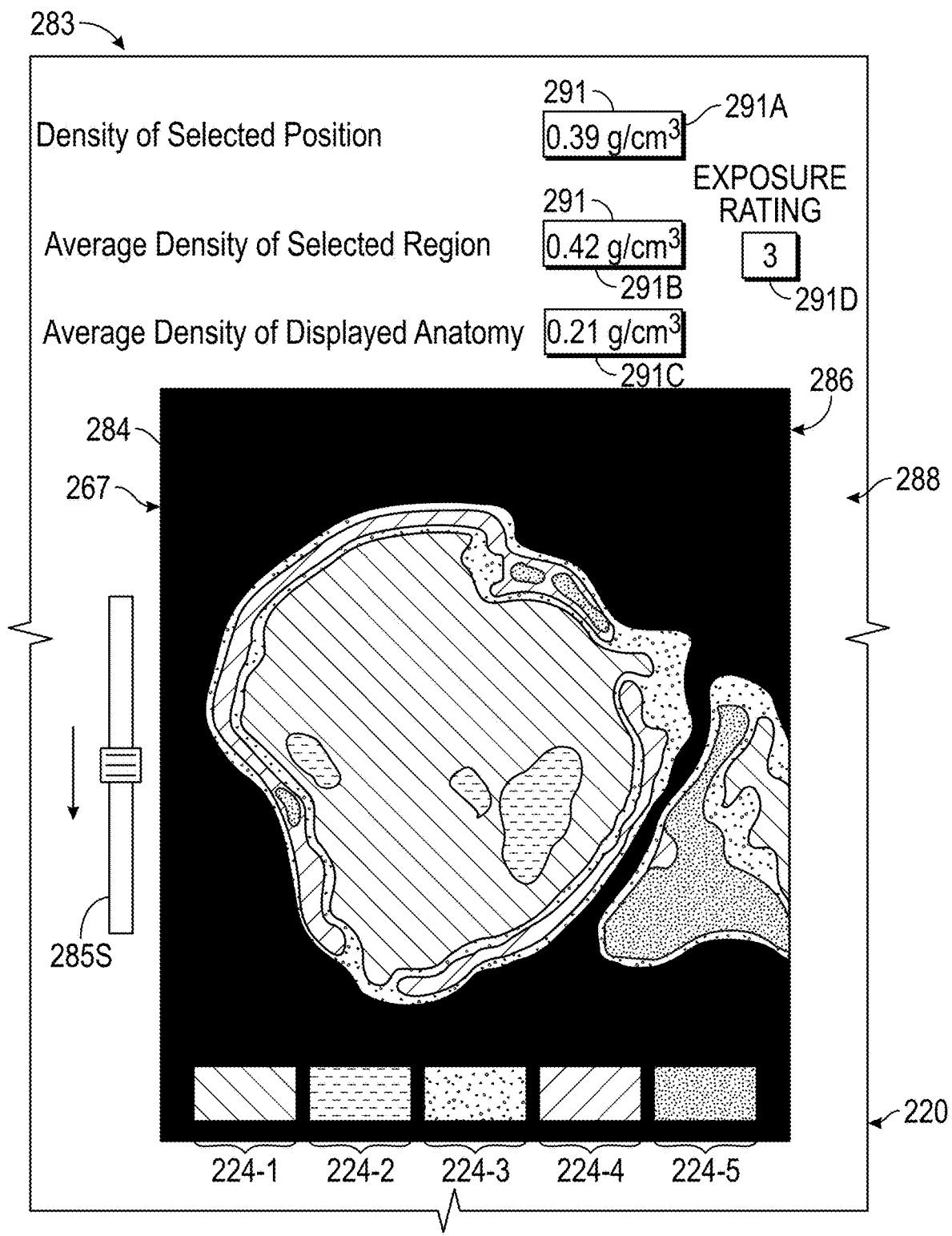

Referring to FIG. 16A, with continuing reference to FIGS. 11-12, the comparison module 280 may be configured to cause the display module 278 to display one or more indicators associated with the respective image(s) 267 in the user interface 283. Exemplary indicators may include one or more parameters associated with the assigned radiodensity values, which may be displayed by respective graphic(s) 291. The graphics 291 may overlay, or be arranged adjacent to, the respective display window 284 of the user interface 283, for example.

Figure 16B:
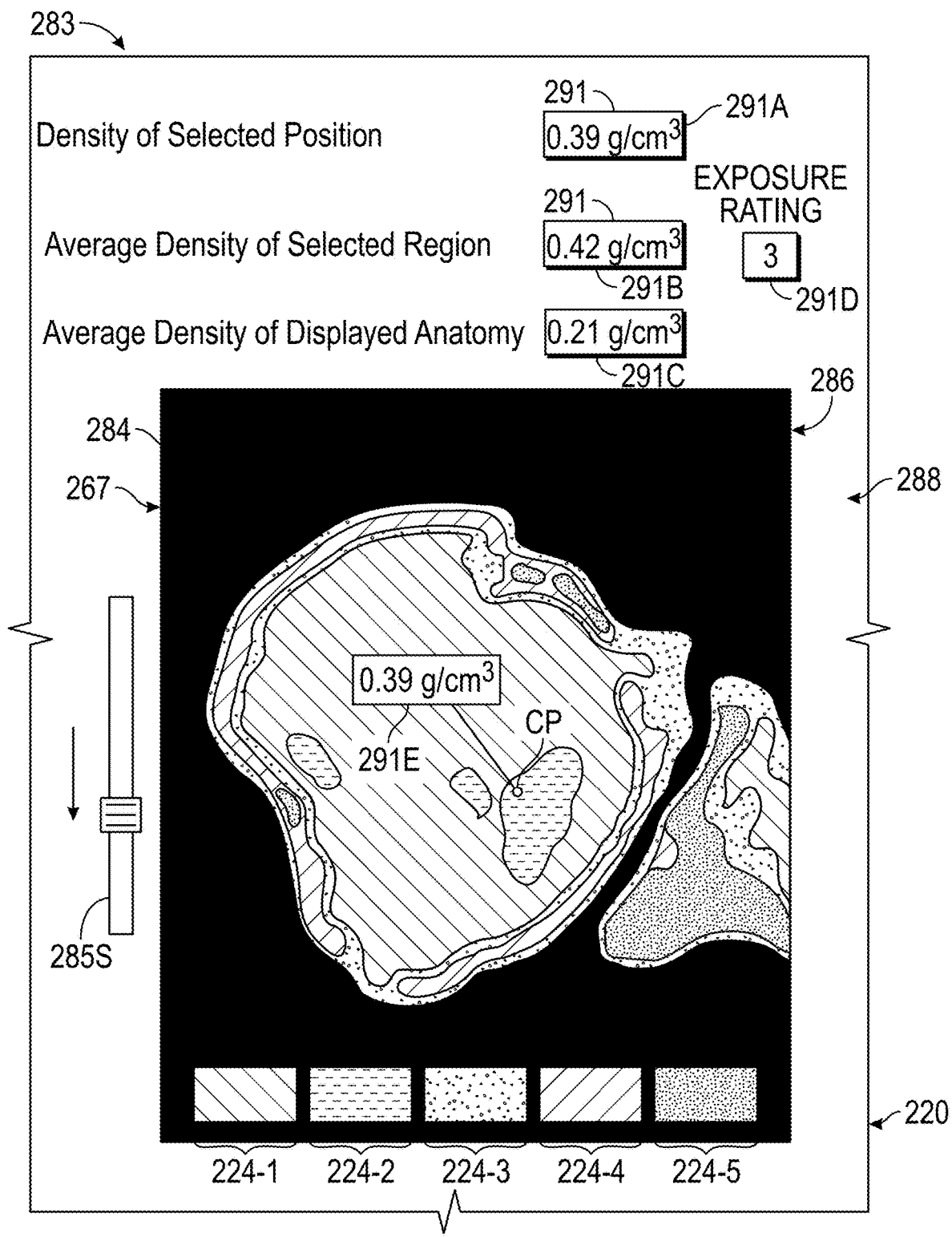

The graphics 291 may include the individual assigned radiodensity value of a single position in the image 267 selected by the surgeon or other user, as illustrated by graphic 291A. The graphics 291 may include an average of the assigned radiodensity values corresponding to a subset of the positions in the image 267 as illustrated by graphic 291B. The subset of positions may be selected in response to user interaction with the user interface 283, such as selecting a localized region of the image 267 in the display window 284. In implementations, the density of the selected position may be displayed in a graphic 291E such as a pop-up box coupled to a cursor position CP, as illustrated in FIG. 16B. The cursor position CP may hover over or otherwise be situated in the display window 284 in response to user interaction utilizing an input device such as a mouse or touch screen. The cursor position CP may be associated with a single position in the display window 284 or a localized region within the display window 284, such as an area within a predefined radius from the selected position. The graphics 291 may include an average of the assigned radiodensity values corresponding to all of the positions of the patient anatomy 286 in the image 267, as illustrated by graphic 291C. In implementations, the spatial module 279 is configured to automatically set the localized region and/or determine the patient anatomy based on determining one or more anatomical features in the image 267, such as a cortical wall or cancellous region surrounded by the cortical wall and various landmarks. Various techniques may be utilized to determine the anatomical features, such as edge detection techniques, which may be based on the assigned radiodensity values.

Figure 17:
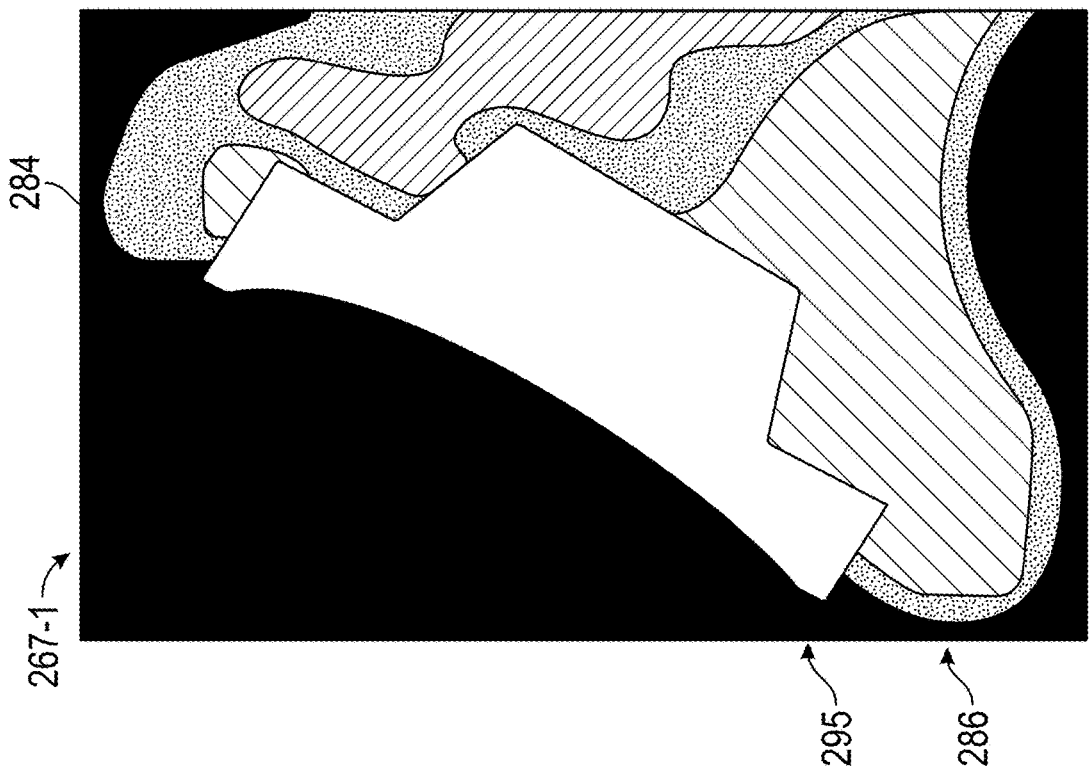

The display module 278 may be configured to display in the user interface 283 the calibrated image 267 and an indicator in the form of a visual gradient 288 superimposed on one or more (or each) of the positions in the image 267 according to the assigned radiodensity values. The visual gradient 288 may be defined by the predetermined radiodensity values associated with the density members 224. The visual gradient 288 may be a visual contrast such as shading or a color gradient in which respective color values are assigned with respect to the predetermined radiodensity values of the density members 224. The visual gradient 288 is depicted as hatching in FIG. 16A for illustrative purposes. The visual gradient 288 may be established by discrete values corresponding to the density members 224 or may be a continuum across the predetermined density range of the associated calibration object 220. The display module 278 may be configured to display the calibrated images according to a translation between the greyscale pixel values and mapped color values in the color mapping. The color gradient may be established such that matching ranges of color are placed in regions of corresponding density. For example, assigned density values in a range of about 0-300 HU may be displayed in a first color range (e.g., black or blue), assigned density values in a range of about 300-500 HU may be displayed in a second color range (e.g., green), assigned density values in a range of about 500-900 HU may be displayed in a third color range (e.g., red), assigned density values in a range of about 900-1800 HU or more narrowly about 1500-2000 HU may be displayed in a fourth color range (e.g., orange), assigned density values in a range of about 1800-2000 HU may be displayed in a fifth color range (e.g., yellow), and assigned density values in a range of about 1800-3100 HU may be displayed in a sixth color range (e.g., pink, or white as illustrated in FIG. 17). The hatching in FIG. 16A may illustrate each of the exemplary color ranges associated with bone tissue, with lower radiodensities illustrated in black shading. Each of the color ranges may include color values associated with the assigned radiodensity values such that the color range encompasses differences in intensity (e.g., chrominance) and/or brightness (e.g., luminance). In implementations, ranges of assigned density values may be displayed in respective color ranges (e.g., ranges 0-300, 300-500, 500-900, 900-1800, 1800-2000, and 2000-3100 HU), while the positions may be shaded according to a common shading range to indicate a continuum of radiodensity values (e.g., across a range of 0-3100 HU).

The display module 278 may be configured to filter from the visual gradient 288 any of the assigned radiodensity values below (or above) at least one predetermined threshold, as illustrated by the lack of hatching for zones surrounding the bone tissue in FIG. 16A. The predetermined threshold may correspond to the minimum value of the predetermined density range of the calibration object 220 or may be set by the surgeon in response to user interaction with the user interface 283. Values of the graphics 291 may be generated based on the predetermined threshold(s) to exclude positions outside of the range. The disclosed filtering techniques may be utilized to observe localized regions of the patient anatomy 286 to determine or infer bone density and/or bone quality, for example.

Figure 16C:
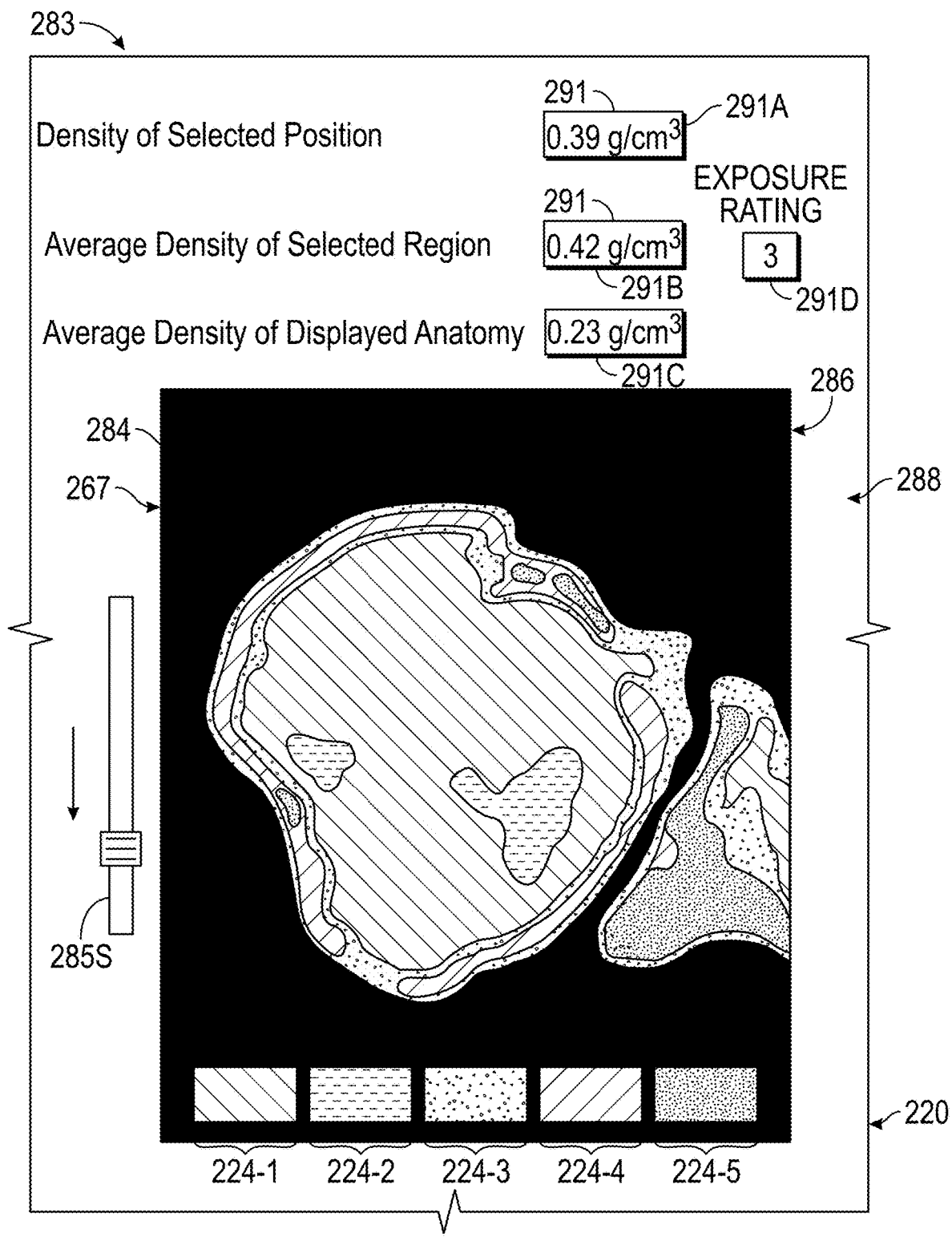

The user interface 283 may include one or more objects 285 that facilitate the display of different positions associated with the patient anatomy in the acquired images 267, such as a slider bar 285S adjacent to the respective display window 284. The user may interact with the slider bar 285S to adjust a depth of the patient anatomy 286 displayed in the display window 284, with each depth associated with one or more respective images 267. For example, the image 267 of FIG. 16A may be associated with a first depth or position of the patient anatomy 286, and the image 267 of FIG. 16C may be associated with a second, different depth or position of the patient anatomy. Each depth may be established relative to an axis extending perpendicular (e.g., out of page) to a plane of the display window 284. Each of the images 267 may be displayed utilizing any of the indicators and techniques disclosed herein including a visual gradient 288 superimposed on one or more (or each) of the positions in the image 267 according to the assigned radiodensity values. One or more aspects of the visual gradient 288 of FIG. 16A may differ from the visual gradient 288 of FIG. 16C, which may correspond to the respective radiodensities associated with the patient anatomy 286 at the respective depths or positions.

In implementations, the user interface 283 may include one or more objects 293 associated with the histogram graph 287 that may be utilized to filter or isolate particular positions in the image 267, as illustrated in FIG. 13. In implementations, the objects 293 include a first slider 293-1 and a second slider 293-2 which may be associated with lower and upper boundaries or limits of a selectable range. The first slider 293-1 may be associated with a first value V1, and the second slider 293-2 may be associated with a second value V2. The first and second values V1, V2 may be respective HU values establishing a subrange, including any of the HU values and ranges disclosed herein. The surgeon or other user may interact with the sliders 293-1, 293-2 to set the respective values V1, V2 to filter the assigned radiodensity values in the image 267. Indicators such as the visual gradients may be displayed in the display window 284 for positions having assigned density values within the selected subrange established between the values V1, V2 of the sliders 293-1, 293-2, which may encompass one or more of the predetermined density values of the density members 224, while indicators may be excluded for positions having assigned density values falling outside of the selected subrange. The excluded positions may be displayed in black (or white) shading or in the same manner as the lowest (or highest) assigned radiodensity value in the image 267, for example.

Referring to FIG. 17, with continuing reference to FIGS. 11 and 16, the surgeon may utilize the system 250 to evaluate changes in the patient anatomy 286 subsequent to a surgical procedure. For example, the surgeon may position an implant 295 at the surgical site during the surgical procedure. One or more images 267 may be captured or acquired of the patient anatomy 286 with the implant 295 installed at the surgical site, as illustrated by the image 267-1 of FIG. 17. Image 267-1 may be a portion of the image 267 of FIG. 16A, for example. The calibration object 220 is omitted from FIG. 17 for illustrative purposes.

Figure 18:
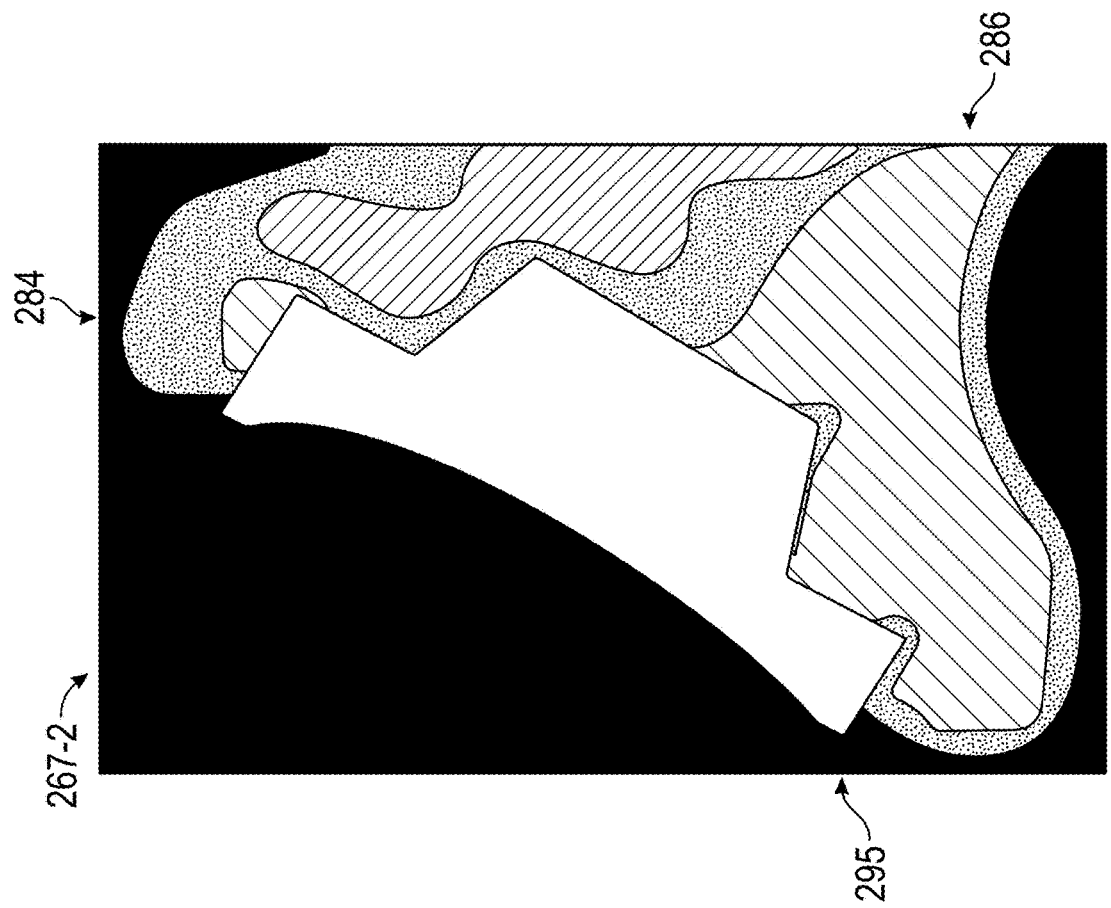

Referring to FIG. 18, with continuing reference to FIGS. 11 and 17, a second image 267-2 of the same patient anatomy 286 may be captured or acquired subsequent to the first image 267-1, such as about six to twelve months after the first image 267-1 or surgical procedure.

The comparison module 280 may be configured to determine a difference between the assigned radiodensity values of at least a subset, or each, of positions common between the first image 267-1 and second image 267-2. The same calibration object 220 may be captured in both of the images 267-1, 267-2 (see, e.g., FIG. 16A), although the calibration blocks 220 may differ.

Figure 19:
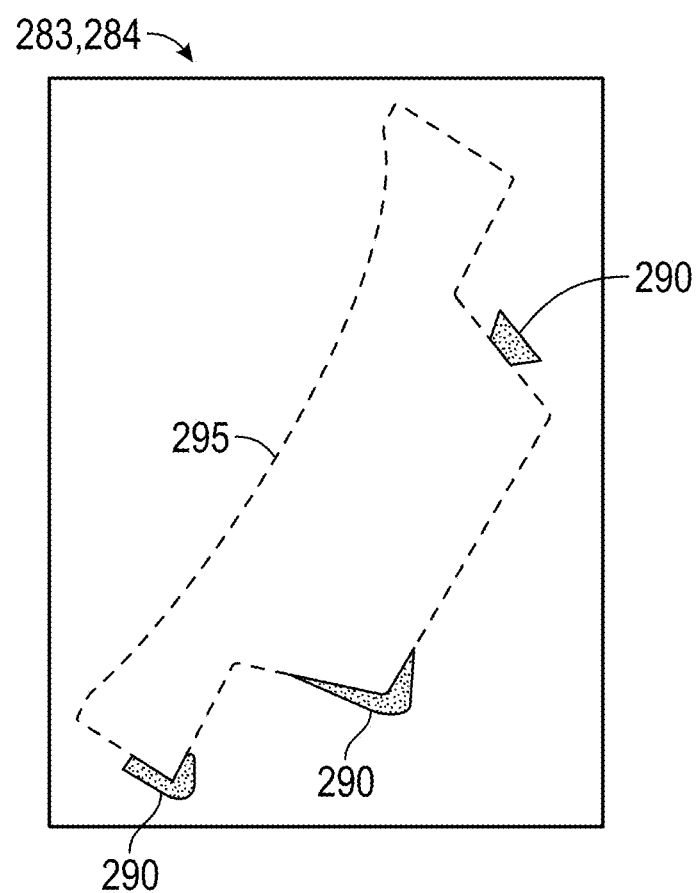

Referring to FIG. 19, with continuing reference to FIGS. 11 and 17-18, the display module 278 may be configured to display in the display window 284 of the user interface 283 at least one indicator 290 according to the difference in the assigned radiodensity values. The indicator 290 may be superimposed on positions associated with differences in the assigned radiodensity values. For example, the display module 278 may be configured to display the indicator 290 in the display window 284 only for positions in the second image 267-2 having an assigned radiodensity value that differs from the assigned radiodensity value of the respective position in the first image 267-1 (implant 295 shown in dashed lines for illustrative purposes).

Figure 20:
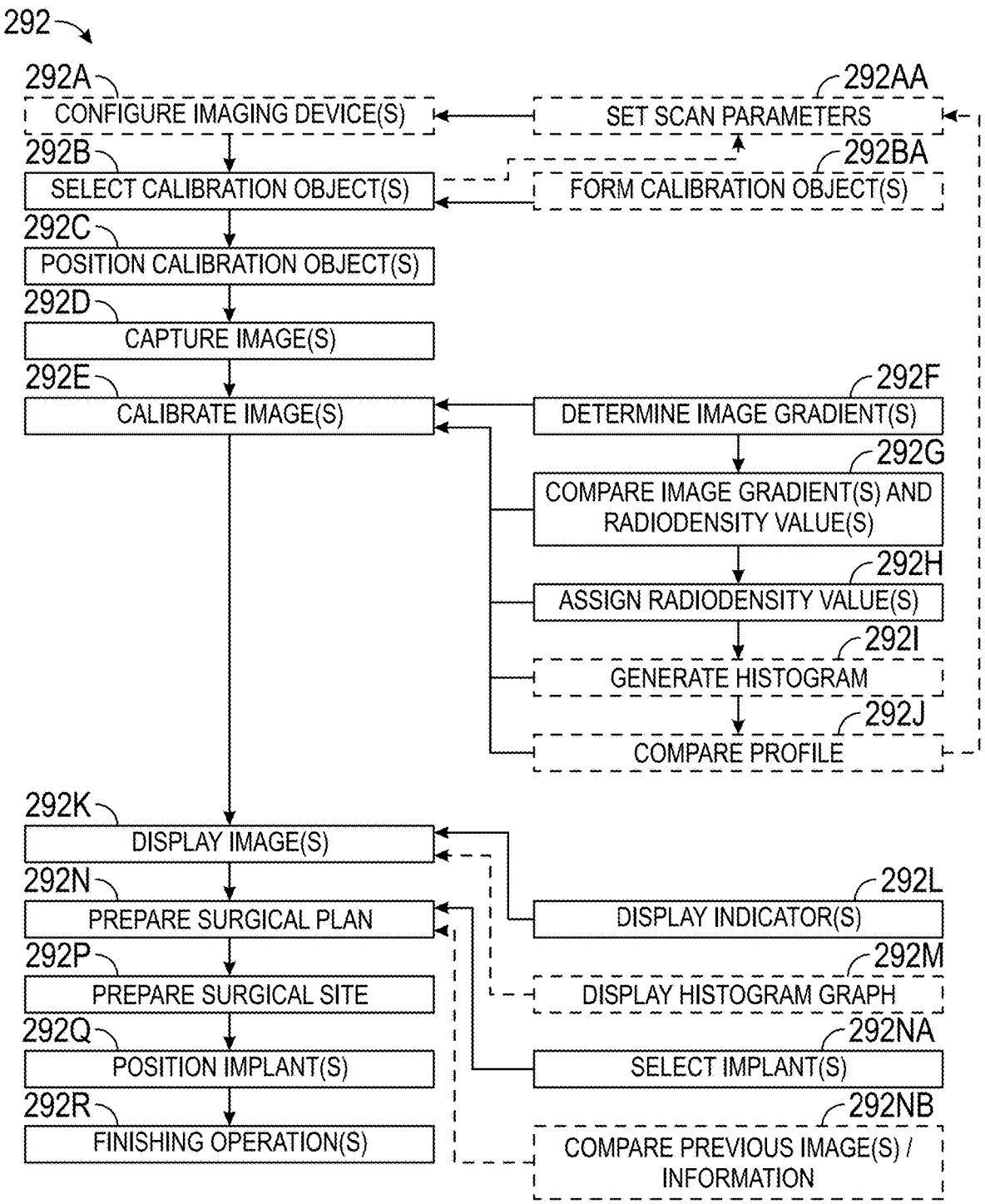
FIG. 20 illustrates an exemplary method of planning an orthopaedic procedure.

FIG. 20 illustrates an exemplary method of planning an orthopaedic procedure, including calibrating images of anatomy, in a flowchart 292. The method may be utilized pre-operatively, intra-operatively and/or post-operatively to create, edit, execute and/or review a respective surgical plan. The method may be utilized to perform an arthroplasty for restoring functionality to shoulders and other joints. Although the method 292 primarily refers to a shoulder reconstruction, it should be understood that the method and disclosed implants may be utilized in other locations of the patient and other surgical procedures, including any of the joints and procedures disclosed herein. The method 292 may be utilized with any of the planning systems disclosed herein. Fewer or additional steps than are recited below could be performed within the scope of this disclosure, and the recited order of steps is not intended to limit this disclosure. Reference is made to the planning system 250 for illustrative purposes.

At step 292A, one or more imaging devices 261 may be configured by the surgeon or another user. The imaging device 261 may be configured to capture or acquire image(s) 267 according to one or more scan parameters, including any of the scan parameters disclosed herein.

At step 292B, one or more calibration objects 220 may be selected for calibration of images of the patient anatomy. The calibration objects 220 may include any of the calibration objects disclosed herein, which may include one or more density members having radiodensities and respective predetermined radiodensity values.

Step 292B may include forming the selected calibration object(s) 220 at step 292BA. Forming each of the selected calibration objects 220 may be performed utilizing any of the techniques disclosed herein, such as printing the calibration object 220 utilizing a three-dimensional (3D) printer, as illustrated by the calibration object 20 of FIG. 4. The calibration object 220 may be printed or otherwise formed according to a construct or profile associated with a respective record 281 selected from the database 266. The construct may approximate a geometry of patient anatomy of the patient or another patient associated with a prior case. For example, the construct may be a porous scaffold, such as the scaffold 134 of FIG. 9, and may approximate a density of cortical bone and/or cancellous bone associated with the respective patient.

Step 292BA may include accessing one or more records 281 in the database(s) 266 to obtain a respective profile of the selected calibration object 220, including the associated geometry and predetermined radiodensity values of the main body 222 and density members 224. The information including the predetermined radiodensity values may be arranged in one or more lookup tables in the record(s) 281. In implementations, step 292B may include automatically selecting the calibration object(s) 220 based on the imaging device(s) 261 identified in step 292A. For example, the database(s) 266 may include one or more records 281 including a profile of each respective imaging device 261. The profile may include values of the scan parameters and other information of the corresponding imaging device(s) 261. Step 292B may include automatically selecting the calibration object 220 based on the scan parameters of the imaging device 261. In implementations, the scan parameters of the selected imaging device 261 may be set at step 292AA based on the calibration object(s) 220 selected at step 292B, which may improve calibration of images 267 acquired by two or more imaging devices 261 when utilizing a common (e.g., single) calibration object 220.

Figure 21:
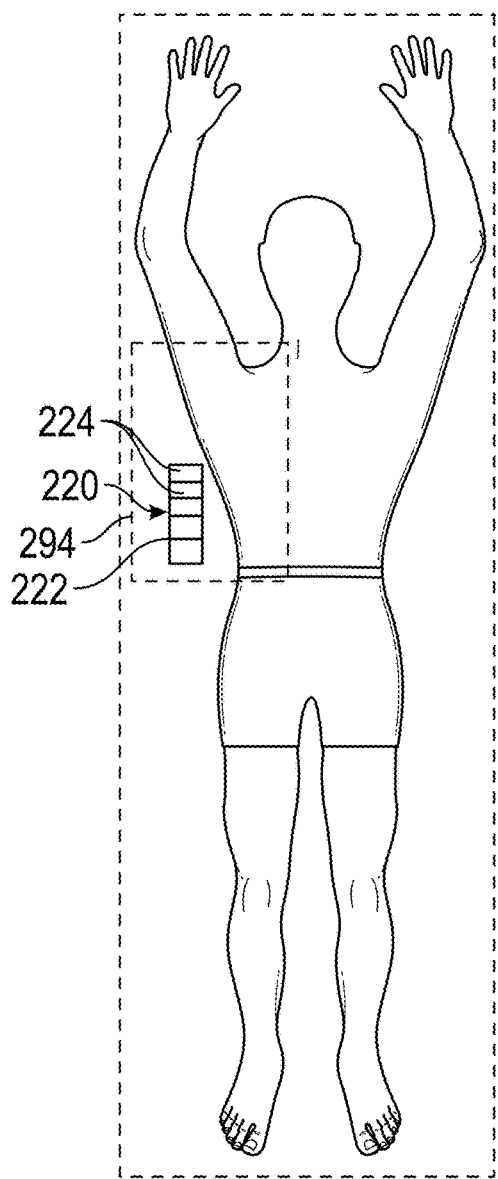
FIGS. 21-22 illustrate calibration objects positioned adjacent to a patient in a scan field of an imaging device.
Figure 22:
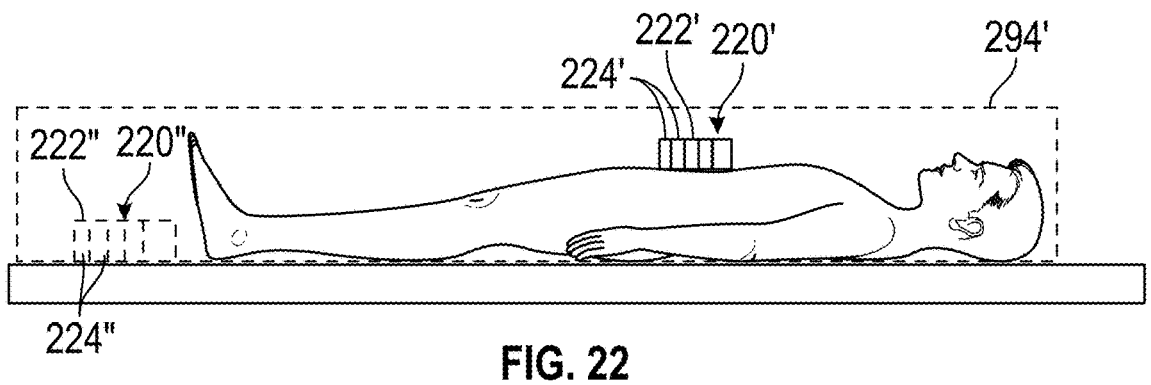

Referring to FIG. 21, with continuing reference to FIGS. 11 and 20, at step 292C a calibration object 220 may be positioned in a scan field 294 of a respective imaging device 261 (294 shown in dashed lines for illustrative purposes). Each calibration object 220 may be positioned at various locations relative to the patient, such as adjacent to the patient as illustrated in FIG. 21 and/or in contact with the patient as illustrated by calibration object 220' in FIG. 22. The selected position(s) of the calibration object(s) 220 may be chosen to reduce a likelihood of interference. Two or more calibration objects 220 may be positioned in the scan field 294 of the imaging device 261 and captured in the same image 267, as illustrated by calibration objects 220', 220" in the scan field 294' of FIG. 22 (220" shown in dashed lines for illustrative purposes). The calibration objects 220', 220" may be the same or may have different predetermined radiodensity values for one or more, or each, of the respective density members 224', 224".

At step 292D, one or more images 267 are captured by the imaging device 261. The images 267 may be captured of the patient anatomy together with the calibration object 220 in the scan field 294. The patient anatomy may include a cortical wall surrounding a cancellous region of a bone associated with a joint, as illustrated in FIG. 13 (see also FIG. 16A).

At step 292E, one or more of the images 267 are calibrated or standardized utilizing the calibration block(s) 220. Step 292E may include determining one or more image gradients at step 292F. Each of the image gradients may be based on a comparison of a pixel value at a respective position in the respective image 267 and a pixel value at one or more respective positions along the density members 224 in the image. Step 292E may include comparing the image gradients to the respective predetermined radiodensity value(s) of the density member(s) 224 associated with the pixel value(s) at step 292G. In implementations, the comparison step 292G is performed for only one of the density members 224. In other implementations, the comparison step 292G is performed for two or more, or each, of the density members 224, which may improve accuracy in determining or inferring the actual radiodensity of the respective position along the patient anatomy in the image 267.

At step 292H, radiodensity value(s) may be assigned to the position(s) in the respective image 267, including along the patient anatomy, based upon the comparison performed at step 292G. The radiodensity values may be assigned utilizing any of the techniques disclosed herein.

At step 292I, a histogram graph may be generated. The histogram graph may comprise a frequency of the radiodensity values assigned at step 292H. The histogram graph may be generated for all positions of the patient anatomy in the respective image 267, or may be generated for a selected subset of the positions.

At step 292J, a profile of the histogram graph may be compared to a predetermined profile. Setting the scan parameters of the imaging device 261 at step 292AA may occur in response to the comparing the profiles at step 292J prior to subsequent image acquisition. The histogram graph may be utilized to adjust a gain of the respective image 267 to generate a pseudo-color calibrated image.

Step 292E may include storing the calibrated image(s) 267 in the database 266. Each calibrated image 267 may be associated with a respective record 281, which may be linked to the record 281 of the corresponding uncalibrated image 267.

At step 292K, the image(s) 267 may be displayed in one or more display windows 284 of the user interface 283, as illustrated in FIGS. 12-13. Step 292K may occur subsequent to step 292E such that the pixel values and other information in the image(s) 267 are calibrated utilizing the calibration block(s) 220.

Step 292K may include displaying one or more indicators associated with the respective image(s) 267 in the user interface 283 at step 292L. Exemplary indicators may include one or more parameters associated with the assigned radiodensity values, as illustrated in FIG. 16A. For example, step 292K may include displaying the assigned radiodensity value(s) in the user interface 283 for one or more positions in the respective image 267 utilizing the graphics 291. The user interface 283 may be configured to display the individual assigned radiodensity value of a position selected by the surgeon or other user, as illustrated by graphic 291A, or may be configured to display an average of the assigned radiodensity values corresponding to a subset of positions or all positions of the patient anatomy in the respective image 267, as illustrated by graphics 291B, 291C.

Other exemplary indicators may include a visual contrast between the assigned radiodensity values associated with the positions in the image 267 of the patient anatomy. Step 292L may include displaying in the display window(s) 284 of the user interface 283 the image(s) 267 and a visual contrast in the form of a visual gradient superimposed on the one or more positions along the patient anatomy according to the assigned radiodensity values, as illustrated in FIG. 16A. The visual gradient may be defined by the predetermined radiodensity values associated with the density members 224 of the calibration object 220 utilizing any of the techniques disclosed herein.

Step 292AA may occur in response to a previous iteration of the calibrating step 292E. For example, setting the scan parameters of the imaging device 261 may occur subsequent to one or more previous images 267 being calibrated at step 292E. Utilizing the techniques disclosed herein, actual densities of the tissue captured in the subsequent images may be more precisely determined or inferred.

Step 292K may include displaying one or more histogram graphs in the user interface 283 adjacent to the respective image 267 at step 292M, as illustrated by the histogram graph 287 of FIG. 13.

Step 292L may include displaying one or more indicators in the user interface 283 relating to an exposure (e.g., over-exposure or under-exposure) of the image(s) 267, such as an exposure rating as illustrated by graphic 291D in FIG. 16A. The surgeon or other user may cause one or more of the scan parameters to be adjusted at step 292AA based on the information conveyed by the graphic 291D and/or histogram graph 287, and one or more of the steps of the method 292 may be repeated including capturing subsequent image(s) 267 at step 292D and calibrating the subsequent image(s) 267 at step 292E.

At step 292N, the surgeon may prepare a surgical plan for the patient. The surgeon may perform one or more steps in preparing the surgical plan in response to the calibrated image(s) 267 and various information presented or otherwise conveyed in steps 292K, 292L and/or 292M. Preparing the surgical plan may include selecting one or more implants at step 292NA. Selecting each implant may be based on information relating to the image(s) 267 that is displayed or otherwise conveyed to the surgeon during step 292K. For example, the surgeon may select an implant based on type, size, etc. based on the information. Step 292N may include determining one or more procedures to prepare the surgical site, such as a resection plane and resection angle for resecting a bone prior to receiving the implant.

At step 292P, the surgeon may prepare the surgical site for receiving the implant. Step 292P may include one or more cutting, reaming and drilling operations, for example.

At step 292Q, the selected implant(s) may be positioned at the surgical site. Each selected implant may be positioning along the patient anatomy based on the visual gradient and other indicator(s) displayed in the user interface 283.

One or more finishing operations may be performed at step 292R. Exemplary finishing operations may include fastening or otherwise securing the selected implant with one or more fasteners, and closing any incisions.

The surgical site may be evaluated upon completion and subsequent to the surgical procedure. Step 292D may include capturing the patient anatomy, implant(s) and calibration block(s) 220 in one or more image(s) at different times. Step 292N may include comparing the image(s) 267 and other information conveyed to the surgeon with image(s) 267 and other information previously conveyed to the surgeon or otherwise obtained. For example, step 292D and any of the other steps of method 292 may be repeated for different time periods, such as during or shortly after completion of the surgical procedure (e.g., a first time) and again approximately six to twelve months after completion of the procedure (e.g., a second, different time). Step 292E may include determining a difference between the assigned radiodensity values of one or more positions common between the prior and subsequent image(s) 261 captured at step 292D. Step 292L may include displaying in the user interface 283 at least one indicator superimposed on the one or more common positions in the subsequent image(s) 267 according to the difference in the assigned radiodensity values utilizing any of the techniques disclosed herein (see, e.g., FIG. 19). The surgeon may compare the density values presented by graphics 291 and other indicators associated with the calibrated images 267 to determine or infer changes in bone density and bone quality, which may be utilized in determining whether a subsequent surgical procedure or treatment for the patient may be indicated.

Figure 23:
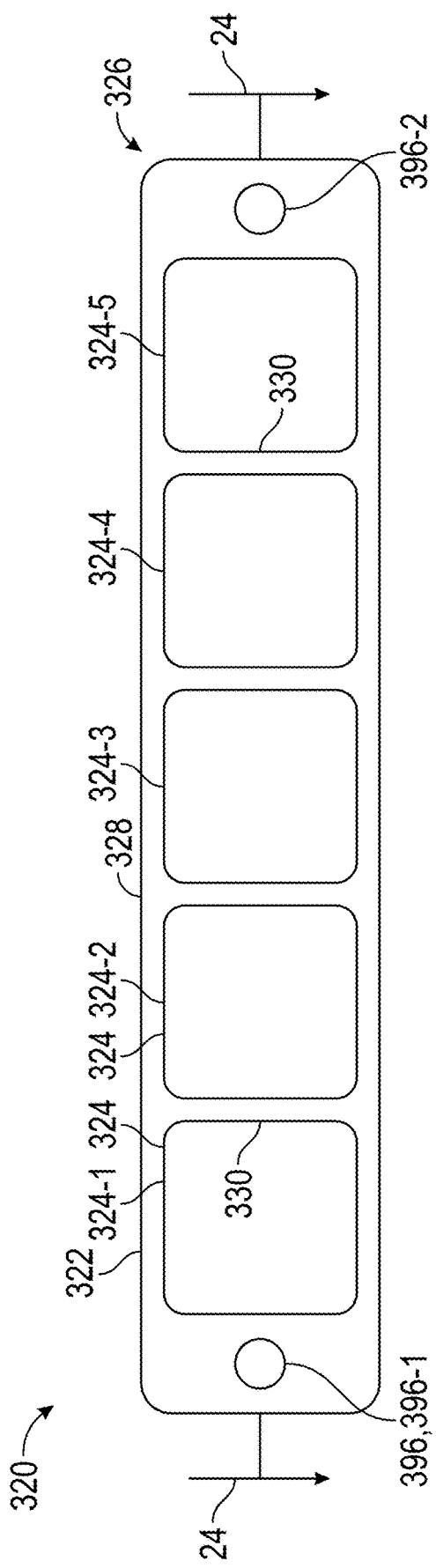
FIGS. 23-25 illustrate another exemplary calibration object.
Figure 24:
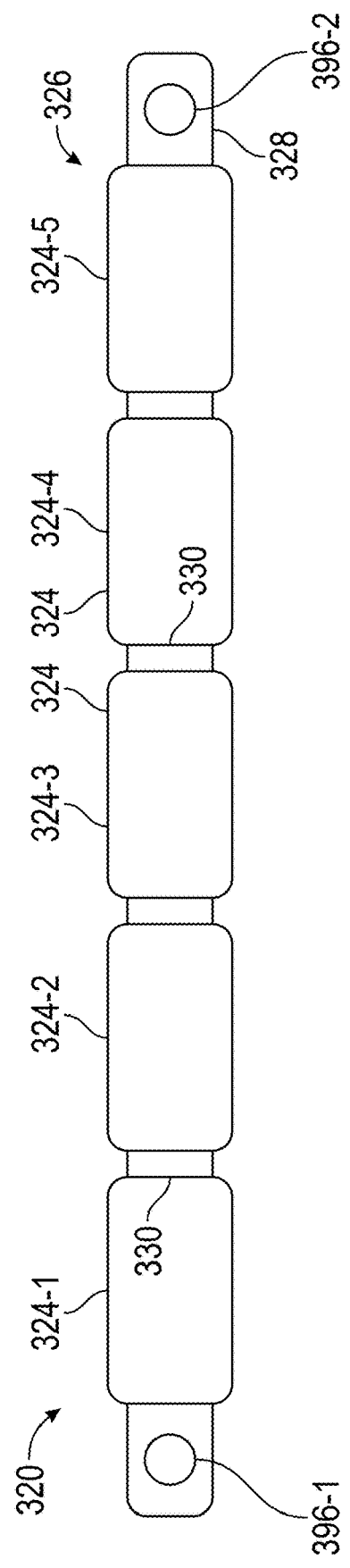
Figure 25:
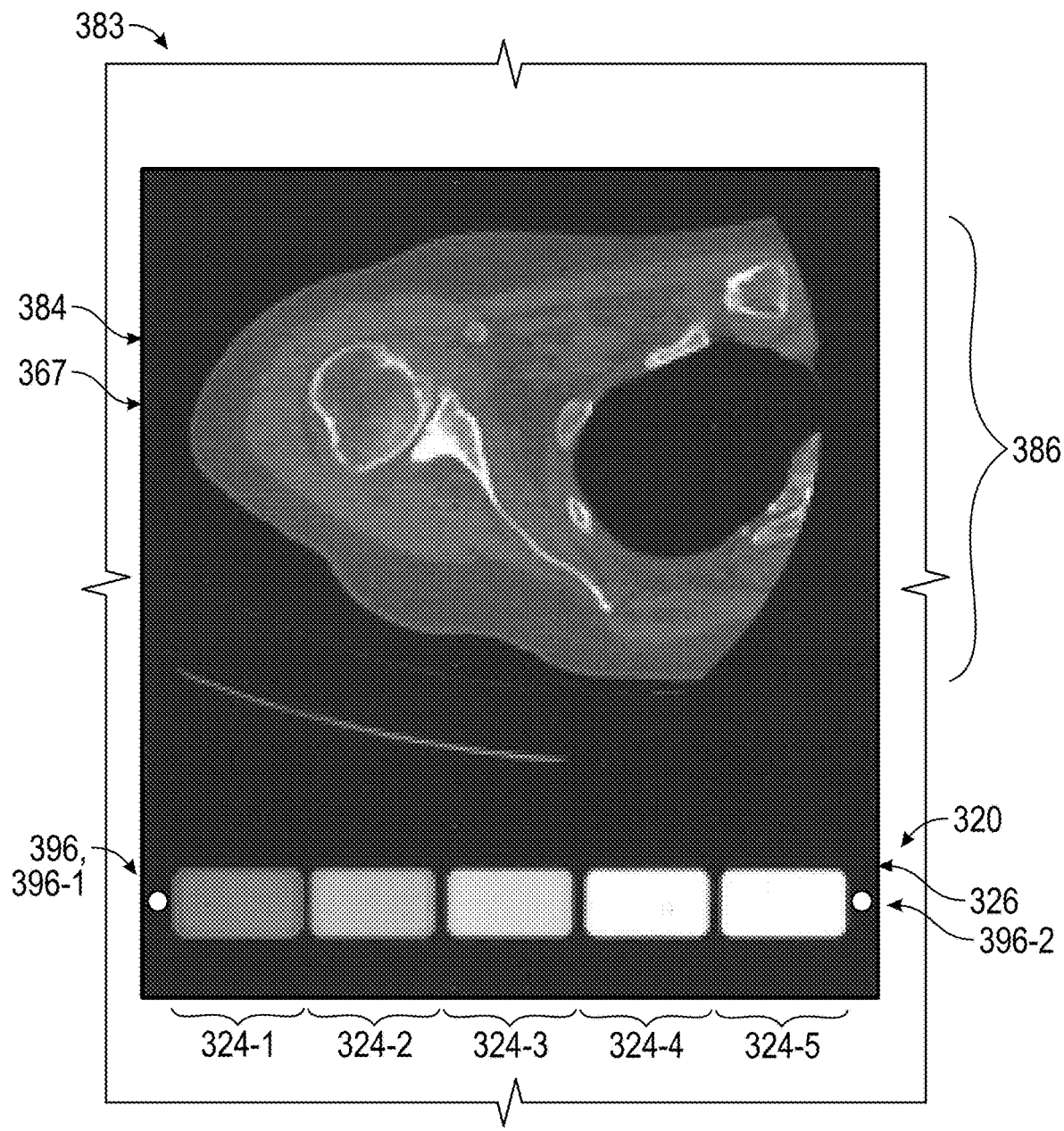

FIGS. 23-24 illustrate another exemplary calibration object 320. The calibration object 320 may be utilized with any of the planning systems and techniques disclosed herein including the planning system 250 and method 292. FIG. 25 illustrates the calibration object 320 in an acquired image 367 relating to patient anatomy. The acquired image 367 may be presented or displayed in a display windows 384 of a graphical user interface 383. The graphical user interface 383 and display window 384 may be incorporated into the planning system 250. Reference is made to the planning system 250 and method 292 for illustrative purposes.

The calibration object 320 may include a main body 322 and one or more density members 324. The density members 324 may be distributed in an array 326 along the main body 324.

The calibration object 320 may include one or more registration members 396. The registration members 396 may be utilized for determining a position of each of the density members 324 in one or more acquired images 367. The calibration object 320 including the main body 322, density members 324 and registration members 396 may be formed utilizing any of the techniques, materials and radiodensities disclosed herein. In implementations, the registration members 396 may be printed or otherwise formed together with the main body 322 and density members 334. The registration members 396 may be formed in or along the main body 322 or another portion of the calibration object 320.

The registration members 396 may be positioned at predetermined distances from the density members 324. In implementations, the registration members 396 include a pair of registration members 396 (indicated at 396-1, 396-2). The registration members 396-1, 396-2 may be established or positioned on opposed sides of the array 326 of the density members 324. In other implementations, one or more of the registration members 396 are situated between the density members 324. Although only two registration members 396 are shown, it should be understood that fewer or more than two registration members 396 may be utilized.

A volume of each of the registration members 396-1, 396-2 may be associated with a predetermined radiodensity value. The radiodensity value of each registration member 396 may be greater than at least some or each of the predetermined radiodensity values of the main body 322 and density members 324. The registration members 396 may be constructed with predetermined radiodensity values such that the registration members 396 are substantially radiopaque, as illustrated in the image 367 of FIG. 25.

The registration members 396 may have various geometries which may be selected to facilitate determining a position of the registration members 396 in acquired images. The registration members 396 may have a substantially spherical geometry, as illustrated in FIGS. 23-25. Other exemplary geometries may include non-naturally occurring geometries such as substantially cube-shaped, cylindrical, pyramidal, prismatic and other complex geometries.

The spatial module 279 of the planning environment 262 (FIG. 11) may be configured to query one or more corresponding entries 281 in the database 266 indicating a geometry of the registration members 396, a predetermined distance between the registration members 396 and/or predetermined distances between the registration members 396 and the respective density members 324. The spatial module 279 may be configured to determine the one or more respective positions along the density members 324 in the acquired image(s) 367 in response to identifying respective positions of the registration members 396 in the acquired image(s) 367. The spatial module 279 may be configured utilizing various techniques to determine the positions of the registration members 396, including edge detection and other object recognition techniques.

The spatial module 279 may be configured to compare a distance between the registration members 396 in the acquired image 367 to the predetermined distance to validate identification of the registration members 396 in the acquired image 367. The spatial module 279 may be configured to normalize the determined distance between the registration members 396 in the acquired image 367 based on the predetermined distance and/or one or more predetermined parameters relating to the imaging device 261. The spatial module 279 may be configured to determine that the calibration object 320 is oriented at an angle relative to the scan field 294 of the imaging device 261 in response to determining that the determined distance between the registration members 396 is less than the predetermined distance indicated in the associated entry 281.

The spatial module 279 may be configured to compare the determined distance between the registration members 396 and the determined distances between one or more of the registration members 396 and the respective density members 324 to determine the positions of the density members 324 in the acquired image(s) 367. The functionality of the spatial module 279 may be incorporated into the method 292 such as step 292E to calibrate acquired images.

The novel planning systems and methods of this disclosure can be incorporated to a practical application by providing improved calibration of images of patient anatomy. Calibration objects may be formed for a corresponding joint and/or procedure, which may be used to more precisely determine or infer radiodensity values and densities of the associated tissue. The calibration information may be displayed to the surgeon and other users for creating, editing and reviewing a surgical plan. Calibrated images may be established at the completion of the surgical procedure and at a later time, such as when bone remodeling is expected to occur, which may be utilized to determine or infer changes in bone density and bone quality. The gathering of this information, including across a post-operative timeframe, may be utilized to aid in therapeutic guidance and targeted treatments to improve bone density and reduce unintended resorption within normal treatment parameters.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A system for calibrating images of anatomy comprising:
   a calibration object including a plurality of density members formed with a main body, wherein a volume of each of the density members and the main body corresponds to a respective predetermined radiodensity value; and
   an imaging system comprising:
   a computing device including a processor coupled to memory, wherein the processor is configured to execute a planning environment including a data module, a display module and a comparison module;
   wherein the data module is configured to receive data corresponding to at least one image of a patient anatomy together with the calibration object from an imaging device;
   wherein the comparison module is configured to determine one or more image gradients, each of the one or more image gradients based on a comparison of a pixel value at a respective position in the at least one image and a pixel value at one or more respective positions along the density members in the at least one image;
   wherein the comparison module is configured to assign a radiodensity value to one or more positions in the at least one image based upon a comparison of the respective one or more image gradients and each respective predetermined radiodensity value; and
   wherein the display module is configured to display in a graphical user interface the at least one image and a visual gradient superimposed on the one or more positions according to the assigned radiodensity values, wherein the visual gradient is defined by the predetermined radiodensity values associated with the density members.

2. The system as recited in claim 1, wherein the at least one image is an X-ray image.

3. The system as recited in claim 2, wherein the imaging device is a computerized tomography (CT) machine.

4. The system as recited in claim 1, wherein the visual gradient is a color gradient in which respective color values are assigned with respect to the predetermined radiodensity values of the density members.

5. The system as recited in claim 1, wherein:
   wherein the display module is configured to display in the graphical user interface a histogram graph comprising a frequency of the assigned radiodensity values corresponding to at least a subset of the one or more positions in the at least one image.

6. The system as recited in claim 1, wherein:
   the at least one image includes a first image and a second image acquired subsequent to the first image;
   the comparison module is configured to determine a difference between the assigned radiodensity values of the one or more positions in the first image and the second image; and
   the display module is configured to display in the graphical user interface at least one indicator superimposed on the one or more positions in the second image according to the difference in the assigned radiodensity values.

7. The system as recited in claim 6, wherein:
   the display module is configured to filter from the visual gradient any of the assigned radiodensity values below at least one predetermined threshold.

8. The system as recited in claim 1, wherein the plurality of density members are distributed in an array along the main body.

9. The system as recited in claim 8, wherein the density members include three or more density members, the respective predetermined radiodensity values being within a predetermined radiodensity range, and wherein the predetermined radiodensity range is greater than or equal to about 300.0 HU, and is less than or equal to about 1800.0 HU.

10. The system as recited in claim 8, wherein:
the calibration object includes a pair of registration members established on opposed sides of the array of the density members; and
the planning environment includes a spatial module configured to determine the one or more respective positions along the density members in the at least one image in response to identifying respective positions of the pair of registration members in the at least one image.

11. A method for calibrating images of anatomy comprising:
printing a calibration object, wherein the calibration object includes a plurality of density members having radiodensities corresponding to respective predetermined radiodensity values;
positioning the calibration object in a scan field of an imaging device;
capturing, by the imaging device, at least one image of a patient anatomy together with the calibration object in the scan field;
determining one or more image gradients, each of the one or more image gradients based on a comparison of a pixel value at a respective position in the at least one image and a pixel value at one or more respective positions along the density members in the at least one image;
comparing the respective one or more image gradients to each respective predetermined radiodensity value;
assigning a radiodensity value to one or more positions in the at least one image based upon the comparing; and
displaying in a graphical user interface at least one indicator relating to the assigned radiodensity values.

12. The method as recited in claim 11, wherein the calibration object includes a pair of registration members established at predetermined positions relative to the radiodensity members, and further comprising:
determining the one or more respective positions along the density members in the at least one image in response to identifying respective positions of the pair of registration members in the at least one image.

13. The method as recited in claim 11, further comprising:
displaying in a graphical user interface the at least one image and the at least one indicator;
wherein the at least one indicator is a visual gradient superimposed on the one or more positions along the patient anatomy according to the assigned radiodensity values, and the visual gradient is defined by the predetermined radiodensity values associated with the density members.

14. The method as recited in claim 13, further comprising:
positioning a selected implant along the patient anatomy based on the visual gradient.

15. The method as recited in claim 11, wherein the imaging device is configured to capture the at least one image according to a plurality of scan parameters, the plurality of scan parameters including an exposure time parameter, a voltage parameter and an amperage parameter, and further comprising:
setting, prior to the capturing step, at least one of the scan parameters in response to a previous iteration of the determining step.

16. The method as recited in claim 15, further comprising:
generating a histogram graph comprising a frequency of the assigned radiodensity values;
comparing a profile of the histogram graph to a predetermined profile; and
wherein the setting step occurs in response to the comparing the profile.

17. The method as recited in claim 11, wherein the patient anatomy includes a cortical wall surrounding a cancellous region of a bone associated with a joint.

* * * * *